(12) United States Patent
Voskian et al.

(10) Patent No.: US 11,045,833 B2
(45) Date of Patent: Jun. 29, 2021

(54) TASK SPECIFIC IONIC LIQUID-IMPREGNATED POLYMERIC SURFACE COATINGS FOR ANTIBACTERIAL, ANTIFOULING, AND METAL SCAVENGING ACTIVITY

(71) Applicant: Massachusetts Institute of Technology, Cambridge, MA (US)

(72) Inventors: Sahag Voskian, Cambridge, MA (US); Cesar de la Fuente Nunez, Somerville, MA (US); T. Alan Hatton, Sudbury, MA (US); Ryan Alex Shaw, Concord, MA (US); Paul Brown, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/482,954

(22) PCT Filed: Feb. 5, 2018

(86) PCT No.: PCT/US2018/016820
§ 371 (c)(1),
(2) Date: Aug. 1, 2019

(87) PCT Pub. No.: WO2018/144984
PCT Pub. Date: Aug. 9, 2018

(65) Prior Publication Data
US 2020/0009611 A1    Jan. 9, 2020

Related U.S. Application Data

(60) Provisional application No. 62/454,299, filed on Feb. 3, 2017.

(51) Int. Cl.
*B05D 1/00* (2006.01)
*A01N 25/04* (2006.01)
(Continued)

(52) U.S. Cl.
CPC .............. *B05D 1/60* (2013.01); *A01N 25/04* (2013.01); *A01N 59/06* (2013.01); *A01N 59/16* (2013.01);
(Continued)

(58) Field of Classification Search
CPC ............ C23C 16/02; C23C 16/50; B05D 3/06
(Continued)

(56) References Cited

U.S. PATENT DOCUMENTS

2007/0104860 A1*  5/2007  Gleason ................ C23C 16/452
                                                                 427/2.14
2012/0073978 A1    3/2012  Malkowsky et al.
(Continued)

FOREIGN PATENT DOCUMENTS

WO    WO-2014179283 A2 *  11/2014  ............... B05D 5/08
WO    WO-2017/016965 A1    2/2017

OTHER PUBLICATIONS

International Search Report and Written Opinion for International Application No. PCT/US2018/016820 dated Mar. 23, 2018.

*Primary Examiner* — Dah-Wei D. Yuan
*Assistant Examiner* — Kristen A Dagenais-Englehart
(74) *Attorney, Agent, or Firm* — Foley Hoag LLP; Dana M. Gordon; Lawrence P. Tardibono

(57) ABSTRACT

Disclosed are polymer-coated surfaces encapsulating task specific ionic liquids (ILs), IL complexes, or oils. Also disclosed are polymer-coated surfaces, wherein the polymer comprises ILs or neutral ethylene diamine compounds. Also disclosed are methods of antimicrobial treatment, metal remediation, and gas absorption using polymer coatings encapsulating ILs, IL complexes, and oils or polymer coatings comprising ILs and neutral ethylene diamine compounds.

24 Claims, 7 Drawing Sheets

Flow of Contaminated Solution

Conductive Substrate with Ionogel

Saturated Ionogel

(51) Int. Cl.
- *A01N 59/06* (2006.01)
- *A01N 59/16* (2006.01)
- *A01N 59/18* (2006.01)
- *A01N 59/20* (2006.01)
- *A61L 29/08* (2006.01)
- *A61L 29/14* (2006.01)
- *A61L 29/16* (2006.01)
- *B01D 53/02* (2006.01)
- *C02F 1/467* (2006.01)
- *C02F 101/20* (2006.01)

(52) U.S. Cl.
CPC ............ *A01N 59/18* (2013.01); *A01N 59/20* (2013.01); *A61L 29/085* (2013.01); *A61L 29/145* (2013.01); *A61L 29/16* (2013.01); *B01D 53/02* (2013.01); *B05D 1/62* (2013.01); *C02F 1/4678* (2013.01); *A61L 2300/102* (2013.01); *A61L 2300/404* (2013.01); *A61L 2300/606* (2013.01); *A61L 2420/02* (2013.01); *B01D 2253/202* (2013.01); *B01D 2257/304* (2013.01); *C02F 2101/20* (2013.01); *C02F 2303/04* (2013.01)

(58) Field of Classification Search
USPC ........................................................ 427/508
See application file for complete search history.

(56) References Cited

U.S. PATENT DOCUMENTS

| | | |
|---|---|---|
| 2012/0156389 A1 | 6/2012 | Kotov |
| 2012/0171094 A1 | 7/2012 | Chinn et al. |
| 2013/0130045 A1 | 5/2013 | Finley |
| 2016/0060277 A1 | 3/2016 | Aduri et al. |

* cited by examiner

Structure of [HHex][Tf2N] complex with copper.

Flow of Contaminated Solution

Conductive Substrate with Ionogel

Saturated Ionogel

Electrolyte

TASK SPECIFIC IONIC LIQUID-IMPREGNATED POLYMERIC SURFACE COATINGS FOR ANTIBACTERIAL, ANTIFOULING, AND METAL SCAVENGING ACTIVITY

RELATED APPLICATIONS

This application is a § 371 national stage application based on Patent Cooperation Treaty Application serial number PCT/US2018/016820, filed Feb. 5, 2018, which claims the benefit of priority to U.S. Provisional Patent Application Ser. No. 62/454,299, filed Feb. 3, 2017.

BACKGROUND

Antibiotic-resistant infections are predicted to kill 10 million people per year by 2050, costing the global economy $100 trillion [1]. Therefore, there is an urgent need to develop alternative technologies to prevent or treat these infections. There are some key areas where antimicrobial agents are employed outside of being active pharmaceutical ingredients (APIs). These include: (i) coatings for high touch areas which are designed to inhibit growth of germs and bacteria (particularly biofilms) on a variety of surfaces, such as door handles, and counters [2]; (ii) coatings for medical devices including prosthetics, implants, catheters, etc. [3]; (iii) in the area of water treatment and purification [4]; and (v) antifouling [5].

To-date antimicrobial coatings have been designed by (i) functionalizing a surface with a polymer or polypeptide [6]; (ii) coating with metals such as copper or silver [7]; (iii) controlling roughness [8]; (iv) incorporation of antibiotics [9]. However, with an increasing resistance to antibiotics and the poor performances of current technologies to completely eradicate biofilm formation there is a need to design ever improved methods.

In addition, the increased use of heavy metals and metalloids in industrial, agricultural and technological applications has led to their wide distribution and persistence in natural water bodies and soil [10, 11]. Elements such as lead, cadmium, nickel, mercury, arsenic and copper may cause multiple organ damage even at low exposure (maximum contaminant level, MCL, of lead is 0.006 mg/L [12]) and are therefore of public health significance [13]. Established technologies to remove metal ions from waste water are varied and include i) ion exchange resins [14, 15], which have high capacities and removal efficiencies, but often prove problematic to regenerate; ii) membrane filtration [16], which is low energy and high efficiency but has problems of fouling; iii) coagulation and flocculation [17, 18], which requires the use of polymers; iv) flotation [19], which requires the use of surfactants; v) adsorption [20], where adsorbents are not always regenerable or are expensive (e.g., activated charcoal); vi) chemical precipitation [21-23], which is low cost but requires the use of a large amount of chemicals and can form sludges; vii) electrochemical treatment [24], which requires large capital investment; viii) solvent (liquid/liquid) extraction, which conventionally requires the use of volatile organic compounds (VOCs).

More recently novel liquid/liquid extractions have been made possible by the development of ionic liquids. Ionic liquids (ILs) are simply salts that are liquid at room temperature. They typically consist of a bulky cation and a small halogenated anion. These salts provide a non-aqueous yet polar medium and therefore have unusual solvent properties. The first ILs designed for heavy metal extraction favorably partitioned metals bound to complexing agents [25], but by appending the cation with metal-ion ligating functional groups, selective extraction of solute metals was achieved directly [26-29]. These new functionalized ILs were named "task specific ILs". However, removal of the metal ions from the IL remains difficult, and recyclability is therefore limited. To date the only removal process reported has been further washing of the IL with organic solvent [30]; an expensive and environmentally unfriendly approach.

A further example is that of gas absorbing function task specific ILs. Gas absorption includes $CO_2$, $SO_2$ and $H_2S$ [31]. In the case of the $H_2S$, ILs bearing Michael acceptors have been demonstrated to scavenge the gas "tagging" the malodourous substance to the ionic matrix [32]. $H_2S$ is produced from degradation of thiamine in chicken and other cooked meats and produces a color change in the meat [33]. The color change does not represent any change in quality of the meat suitable for consumption but causes the meat to be discarded due to consumer preferences.

One approach to address these problems is through the use of functionalized polymer coatings. For example, chemical vapor deposition has been used to create lubricating liquid-impregnated textured coatings to generate low contact angle hysteresis. The work has been disclosed [34] and focuses on superoleophobic or superhydrophobic surfaces with low viscosity liquids but failed to specify the chemical functionality of the contained liquid.

SUMMARY

Accordingly, new methods of coating a surface of an object, a device, or an assembly with functionalized polymers are needed. Disclosed herein are polymer-coated surfaces encapsulating task specific ionic liquids (ILs), IL complexes, or oils. In addition, disclosed herein are polymer-coated surfaces, wherein the polymer comprises ILs or neutral ethylene diamine compounds. The polymer coatings disclosed herein have functionality such as antimicrobial activity to prevent biofilm formation. These thin (10 nm-200 µm) polymer film coatings are prepared via chemical vapor deposition (CVD) and other similar methods (dip coating, etc.).

Further, new methods of antimicrobial treatment are needed. Disclosed herein are methods of antimicrobial treatment using polymer coatings encapsulating ILs, IL complexes, and oils or polymer coatings comprising ILs and neutral ethylene diamine compounds.

In addition, new methods are needed for extracting metals ions from aqueous solution using ILs, and for recycling ILs after the extraction is complete. The present disclosure provides a method to extract metal ions from aqueous solution for water treatment using polymer coatings impregnated with ILs and oils or polymer coatings comprising ILs. The ionic liquids described have a controlled hydrophobic-hydrophilic balance that allows them to dissolve heavy metals at relatively high concentrations (for instance, about 0.20 mol kg$^{-1}$). The metal ions are chelated in the ion-pair region of the IL. In addition, the metal ions may be removed from polymer coatings encapsulating IL complexes or polymer coatings comprising IL complexes, and the IL regenerated, by applying an electrochemical potential.

Also disclosed herein are methods of gas absorption using polymer coatings encapsulating ILs, IL complexes, and oils or polymer coatings comprising ILs and neutral ethylene diamine compounds.

DETAILED DESCRIPTION

Figure 1:
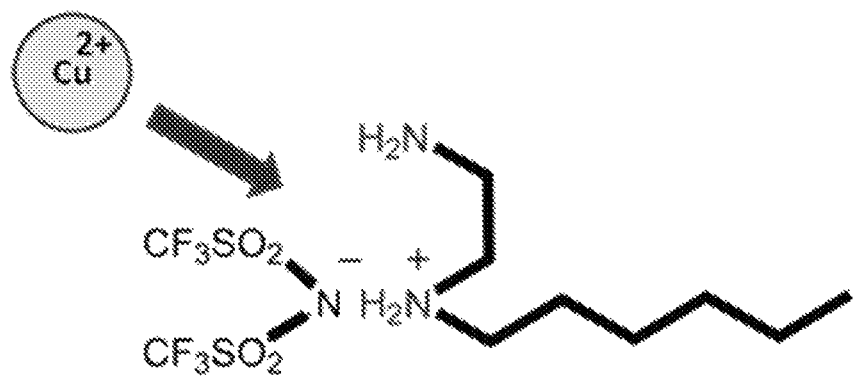
FIG. 1 is a graphical representation of copper binding to the ionic liquid N-hexylethylenediaminium bis(trifluoroethanesulfonyl)amide, [HHex][Tf$_2$N].

This disclosure is based on polymer-coated surfaces impregnated with task specific ionic liquids (ILs), IL complexes, or oils. In addition, disclosed herein are polymer-coated surfaces, wherein the polymer comprises ILs or IL complexes. The polymer coatings disclosed herein have functionality such as antimicrobial activity to prevent biofilm formation, extraction of metals ions from aqueous solution followed by recycling ILs, and gas absorption. These thin (10 nm-200 μm) polymer film coatings are prepared via chemical vapor deposition (CVD).

Methods of antimicrobial treatment using certain ionic liquids (ILs), IL complexes, polymers comprising ILs, and polymers comprising neutral ethylene diamine compounds have been proposed. Pharmaceutically ILs, IL complexes, polymers comprising ILs, and polymers comprising neutral ethylene diamine compounds offer unprecedented ability for preventing biofilm growth. However, the immobilization of these compounds onto surfaces is paramount to avoid leaching and facilitate the functionalization of various devices.

A method to encapsulate the ionic liquid into a polymer matrix is disclosed (often referred to as an ionogel [35]). Because the thin polymer layer is chemically bound to the surface, having been produced via chemical vapor deposition onto a variety of surfaces, the absorbed ionic liquid is fixed in place.

Methods of Forming Polymer Coatings

In another aspect, provided herein are methods of coating a surface of an object, a device, or an assembly with a polymer by CVD. In one aspect, the present disclosure relates to a method of coating a surface of an object, a device, or an assembly, comprising the steps of:

(a) providing in a partially evacuated vessel an object, a device, or an assembly comprising a surface;

(b) heating or irradiating a free radical initiator, thereby producing a gaseous free radical initiator;

(c) introducing into the partially evacuated vessel comprising the object, the device, or the assembly one or more gaseous monomers and the gaseous free radical initiator, thereby forming a cross-linked coating on the surface; and (d) contacting the coating with an ionic liquid mixture comprising an ionic liquid complex comprising an ionic liquid chelated to a metal cation; thereby forming an ionogel on the surface of the object, the device, or the assembly.

In another aspect, the present disclosure relates to a method of coating a surface of an object, a device, or an assembly, comprising the steps of:

(a) providing in a partially evacuated vessel an object, a device, or an assembly comprising a surface, wherein the surface comprises a coating comprising a plurality of reactive moieties;

(b) heating or irradiating a free radical initiator, thereby producing a gaseous free radical initiator;

(c) introducing into the partially evacuated vessel comprising the object, the device, or the assembly one or more gaseous monomers and the gaseous free radical initiator; wherein the reactive moieties react with the monomers and the gaseous free radical initiator, thereby forming a cross-linked coating on the surface; and (d) contacting the cross-linked coating with an ionic liquid mixture comprising an ionic liquid complex comprising an ionic liquid chelated to a metal cation; thereby forming an ionogel on the surface of the object, the device, or the assembly.

In yet another aspect, the present disclosure relates to a method of coating a surface of an object, a device, or an assembly, comprising the steps of:

(a) providing in a partially evacuated vessel an object, a device, or an assembly comprising a surface;

(b) heating or irradiating a free radical initiator, thereby producing a gaseous free radical initiator;

(c) introducing into the partially evacuated vessel one or more gaseous monomers and the gaseous free radical initiator, thereby forming a cross-linked coating on the surface; and (d) contacting the cross-linked coating with an ionic liquid or an oil; thereby forming the coating on the surface of the object, the device, or the assembly.

In still another aspect, the present disclosure relates to a method of coating a surface of an object, a device, or an assembly, comprising the steps of:

(a) providing in a partially evacuated vessel an object, a device, or an assembly comprising a surface, wherein the surface comprises a coating comprising a plurality of reactive moieties;

(b) heating or irradiating a free radical initiator, thereby producing a gaseous free radical initiator;

(c) introducing into the partially evacuated vessel comprising the object, the device, or the assembly one or more gaseous monomers and the gaseous free radical initiator;

wherein the reactive moieties react with the monomers and the gaseous free radical initiator, thereby forming a cross-linked coating on the surface; and (d) contacting the cross-linked coating with an ionic liquid or an oil; thereby forming the coating on the surface of the object, the device, or the assembly.

In a further aspect, the present disclosure relates to a method of coating a surface of an object, a device, or an assembly, comprising the steps of:

(a) providing in a partially evacuated vessel an object, a device, or an assembly comprising a surface, wherein the surface comprises a coating comprising a plurality of reactive moieties;

(b) contacting the surface with an ionic liquid complex comprising an ionic liquid chelated to a metal cation;

(c) heating or irradiating a free radical initiator, thereby producing a gaseous free radical initiator; and (d) introducing into the partially evacuated vessel one or more gaseous monomers and the gaseous free radical initiator, thereby forming an ionogel on the surface of the object, the device, or the assembly.

In one aspect, the present disclosure relates to a method of coating a surface of an object, a device, or an assembly, comprising the steps of:

(a) providing in a partially evacuated vessel an object, a device, or an assembly comprising a surface, wherein the surface comprises a coating comprising a plurality of reactive moieties;

(b) contacting the surface with an ionic liquid;

(c) heating or irradiating a free radical initiator, thereby producing a gaseous free radical initiator; and (d) introducing into the partially evacuated vessel one or more gaseous monomers and the gaseous free radical initiator, thereby forming an ionogel on the surface of the object, the device, or the assembly.

In another aspect, provided herein are methods of coating a surface of an object, a device, or an assembly with a copolymer by chemical vapor deposition (CVD). In some embodiments, the copolymer comprises a plurality of ILs or a plurality of IL complexes.

In some embodiments, provided herein is a method of coating a surface of an object, a device, or an assembly, comprising the steps of:

(a) providing in a partially evacuated vessel an object, a device, or an assembly comprising a surface;

(b) heating or irradiating a free radical initiator, thereby producing a gaseous free radical initiator;

(c) introducing into the partially evacuated vessel comprising the object, the device, or the assembly a first gaseous monomer selected from the group consisting of an acrylate, an acrylamide, an alkene, a silane, and a siloxane compound; a second gaseous monomer, wherein the second gaseous monomer comprises an ionic liquid; and the gaseous free radical initiator, thereby forming a cross-linked coating on the surface of the object, the device, or the assembly.

In some embodiments, provided herein is a method of coating a surface of an object, a device, or an assembly, comprising the steps of:

(a) providing in a partially evacuated vessel an object, a device, or an assembly comprising a surface;

(b) heating or irradiating a free radical initiator, thereby producing a gaseous free radical initiator;

(c) introducing into the partially evacuated vessel comprising the object, the device, or the assembly a first gaseous monomer selected from the group consisting of an acrylate, an acrylamide, an alkene, a silane, and a siloxane compound; a second gaseous monomer, wherein the second gaseous monomer comprises an ionic liquid complex, comprising an ionic liquid chelated to a metal cation; and the gaseous free radical initiator, thereby forming a cross-linked coating on the surface of the object, the device, or the assembly.

In some embodiments, provided herein is a method of coating a surface of an object, a device, or an assembly, comprising the steps of:

(a) providing in a partially evacuated vessel an object, a device, or an assembly comprising a surface;

(b) heating or irradiating a free radical initiator, thereby producing a gaseous free radical initiator;

(c) introducing into the partially evacuated vessel comprising the object, the device, or the assembly a first gaseous monomer selected from the group consisting of an acrylate, an acrylamide, an alkene, a silane, and a siloxane compound; a second gaseous monomer, wherein the second gaseous monomer comprises a neutral ethylene diamine compound represented by the following structural formula III:

(III)

wherein, independently for each occurrence:
$R^1$ is $-(C(R)_2)_n-$;
n is 2, or 3;
$R^2$ is $-(C(R')_2)_m-R''$;
m is 1, 2, 3, 4, 5, 6, 7, 8, 9, or 10; and
R is H, F, $C_1$-$C_3$ alkyl, or $C_1$-$C_3$ fluoroalkyl;
R' is H, F, $C_1$-$C_8$ alkyl, or $C_1$-$C_8$ fluoroalkyl; and
R'' is $C_6$-$C_{10}$ aryl, $C_2$-$C_8$ alkenyl or $C_2$-$C_8$ fluoroalkenyl; wherein each instance of $C_6$-$C_{10}$ aryl is substituted with one, two, three, four or five substituents independently selected from the group consisting of $C_2$-$C_8$ alkenyl or $C_2$-$C_8$ fluoroalkenyl; and the gaseous free radical initiator, thereby forming a cross-linked coating on the surface of the object, the device, or the assembly.

In some embodiments, provided herein is a method of coating a surface of an object, a device, or an assembly, comprising the steps of:

(a) providing in a partially evacuated vessel an object, a device, or an assembly comprising a surface;

(b) heating or irradiating a free radical initiator, thereby producing a gaseous free radical initiator;

(c) introducing into the partially evacuated vessel comprising the object, the device, or the assembly a first gaseous monomer selected from the group consisting of an acrylate, an acrylamide, an alkene, a silane, and a siloxane compound; a second gaseous monomer, wherein the second gaseous monomer comprises a neutral ethylene diamine compound represented by the following structural formula IV:

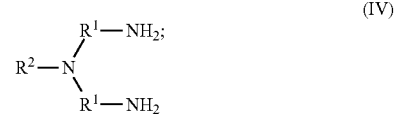

(IV)

wherein, independently for each occurrence:
$R^1$ is $-(C(R)_2)_n-$;
n is 2, or 3;
$R^2$ is $-(C(R')_2)_m-R''$;
m is 1, 2, 3, 4, 5, 6, 7, 8, 9, or 10; and
R is H, F, $C_1$-$C_3$ alkyl, or $C_1$-$C_3$ fluoroalkyl;
R' is H, F, $C_1$-$C_8$ alkyl, or $C_1$-$C_8$ fluoroalkyl; and R" is $C_6$-$C_{10}$ aryl, $C_2$-$C_8$ alkenyl or $C_2$-$C_8$ fluoroalkenyl; wherein each instance of $C_6$-$C_{10}$ aryl is substituted with one, two, three, four or five substituents independently selected from the group consisting of $C_2$-$C_8$ alkenyl or $C_2$-$C_8$ fluoroalkenyl; and the gaseous free radical initiator, thereby forming a cross-linked coating on the surface of the object, the device, or the assembly.

In some embodiments, a neutral ethylene diamine complex is formed, further comprising a metal cation chelated by the neutral ethylene diamine.

In some embodiments, the neutral ethylene diamine is represented by structural formulas III or IV. In some embodiments, the neutral ethylene diamine is N-(4-vinyl)benzylethylene-diamine.

In another aspect, provided herein are methods of coating a surface of an object, a device, or an assembly with a polymer by a continuous coating technique or a roll-to-roll technique. In some embodiments, the coating methods are, for example, CVD, dip-coating, doctor blade coating, and slot die coating. In some embodiments, the coating method is a continuous coating technique, for example, dip-coating. In some embodiments, the coating method is a roll-to-roll technique, for example, doctor blade coating or slot die coating.

In some embodiments of the methods of coating a surface of an object, a device, or an assembly with a polymer, the coating is applied at a speed of about 0.5 ft/min to about 500 ft/min. In some embodiments, the speed is about 1 ft/min to about 250 ft/min. In some embodiments, the speed is selected from the group consisting of about 1 ft/min, about 2 ft/min, about 3 ft/min, about 4 ft/min, about 5 ft/min, about 6 ft/min, about 7 ft/min, about 8 ft/min, about 9 ft/min, about 10 ft/min, about 11 ft/min, about 12 ft/min, about 13 ft/min, about 14 ft/min, about 15 ft/min, about 16 ft/min, about 17 ft/min, about 18 ft/min, about 19 ft/min, about 20 ft/min, about 11 ft/min, about 12 ft/min, about 13 ft/min, about 14 ft/min, about 15 ft/min, about 16 ft/min, about 17 ft/min, about 18 ft/min, about 19 ft/min, about 20 ft/min, about 21 ft/min, about 22 ft/min, about 23 ft/min, about 24 ft/min, about 25 ft/min, about 26 ft/min, about 27 ft/min, about 28 ft/min, about 29 ft/min, about 30 ft/min, about 31 ft/min, about 32 ft/min, about 33 ft/min, about 34 ft/min, about 35 ft/min, about 36 ft/min, about 37 ft/min, about 38 ft/min, about 39 ft/min, about 40 ft/min, about 41 ft/min, about 42 ft/min, about 43 ft/min, about 44 ft/min, about 45 ft/min, about 46 ft/min, about 47 ft/min, about 48 ft/min, about 49 ft/min, about 50 ft/min, about 51 ft/min, about 52 ft/min, about 53 ft/min, about 54 ft/min, about 55 ft/min, about 56 ft/min, about 57 ft/min, about 58 ft/min, about 59 ft/min, about 60 ft/min, about 61 ft/min, about 62 ft/min, about 63 ft/min, about 64 ft/min, about 65 ft/min, about 66 ft/min, about 67 ft/min, about 68 ft/min, about 69 ft/min, about 70 ft/min, about 71 ft/min, about 72 ft/min, about 73 ft/min, about 74 ft/min, about 75 ft/min, about 76 ft/min, about 77 ft/min, about 78 ft/min, about 79 ft/min, about 80 ft/min, about 81 ft/min, about 82 ft/min, about 83 ft/min, about 84 ft/min, about 85 ft/min, about 86 ft/min, about 87 ft/min, about 88 ft/min, about 89 ft/min, about 90 ft/min, about 91 ft/min, about 92 ft/min, about 93 ft/min, about 94 ft/min, about 95 ft/min, about 96 ft/min, about 97 ft/min, about 98 ft/min, about 99 ft/min, about 100 ft/min, about 101 ft/min, about 102 ft/min, about 103 ft/min, about 104 ft/min, about 105 ft/min, about 106 ft/min, about 107 ft/min, about 108 ft/min, about 109 ft/min, about 110 ft/min, about 115 ft/min, about 120 ft/min, about 125 ft/min, about 130 ft/min, about 135 ft/min, about 140 ft/min, about 145 ft/min, about 150 ft/min, about 160 ft/min, about 170 ft/min, about 180 ft/min, about 190 ft/min, about 200 ft/min, about 210 ft/min, about 220 ft/min, about 230 ft/min, about 240 ft/min, and about 250 ft/min. In some embodiments, the speed is about 2 ft/min to about 100 ft/min.

An ionogel is a hybrid compound comprising an interpenetrating network of polymer chains and ILs or IL complexes. In some embodiments, the formation of ionogels allows for immobilization of ILs or IL complexes on a surface of an object, a device, or an assembly. In some embodiments, confinement of ILs or IL complexes allows ILs or IL complexes to retain their chemical functionality under circumstances where an IL or IL complex alone would not. For example, in some embodiments, the ionogel prevents leaching of ILs or IL complexes. In some embodiments, the ionogel comprises a polymer coating encapsulating ILs or IL complexes. In some embodiments, the ionogel comprises a polymer coating impregnated with ILs or IL complexes.

In some embodiments, the ionic liquid mixture further comprises water.

In some embodiments, the ionic liquid mixture further comprises an oil. In some embodiments, the ionic liquid further comprises an oil. For example, an oil includes a hydrophobic oil, a heavy oil, a vacuum pump oil, a silicon oil, a fluorinated oil, an oil mixture comprising a chelating moiety (e.g., a crown ether or a cyclam), peanut oil, cottonseed oil, safflower oil, sesame oil, olive oil, corn oil, or soybean oil.

In some embodiments, the ionic liquid further comprises an organic solvent (e.g., chloroform, dichloromethane, n-hexane, n-heptane, n-decanol, isododecane, n-dodecane, di-2-ethylhexylphosphoric acid, tibutylphosphate, kerosene).

In some embodiments, the ionic liquid further comprises one or more of water, oil, and an organic solvent.

In some embodiments, the reactive moieties are at least one of an acrylate, an alkene, a silane, and a siloxane.

In some embodiments, the ionogel coating further comprises a cellulose derivative.

In some embodiments, the cost of forming the ionogel coating is less than alternatives approaches managing bacterial growth (e.g., antibiotics and metal coatings).

In some embodiments, the ionogel coating is on an article.

Chemical Vapor Deposition

Materials-processing often involves the deposition of films or layers on a surface of a substrate. One manner of effecting the deposition of such films or layers is through chemical vapor deposition (CVD). CVD involves a chemical reaction of vapor phase chemicals or reactants that contain the constituents to be deposited on the substrate. Reactant gases may be introduced into a reaction chamber or reactor, and then decomposed and reacted at a heated surface to form the desired film or layer.

In some embodiments of the methods disclosed herein, the CVD is selected from the group consisting of initiated CVD (iCVD), photoinitiated CVD (piCVD), and initiated plasma-enhanced CVD (iPECVD).

In certain embodiments, CVD takes place in a reactor. In certain embodiments, a variety of monomer species may be polymerized and deposited by CVD; these monomer species are well-known in the art. In certain embodiments, the surface to be coated is placed on a stage in the reactor and gaseous precursor molecules are fed into the reactor; the stage may be the bottom of the reactor and not a separate entity. In certain embodiments, a variety of carrier gases are useful in CVD; these carrier gases are well-known in the art (e.g., nitrogen or argon).

In certain embodiments, the CVD reactor has automated electronics to control reactor pressure and to control reactant flow rates. In certain embodiments, any unreacted vapors may be exhausted from the system.

In certain embodiments, the CVD coating process can take place at a range of pressures from greater than atmospheric pressure to low vacuum. The pressure of the deposition chamber can be selected to provide a suitable environment for coating extremely fine objects.

In certain embodiments, the pressure of the deposition chamber is in the range of about 0.01 Torr to about 800 Torr. In certain embodiments, the pressure of the deposition chamber is in the range of about 0.05 Torr to about 600 Torr. In certain embodiments, the pressure of the deposition chamber is in the range of about 0.075 Torr to about 400 Torr. In certain embodiments, the pressure of the deposition chamber is in the range of about 0.1 Torr to about 200 Torr. In certain embodiments, the pressure of the deposition chamber is in the range of about 0.15 Torr to about 100 Torr. In certain embodiments, the pressure is less than about 50 torr. In certain embodiments, the pressure is less than about 40 torr. In certain embodiments, the pressure is less than about 30 torr. In certain embodiments, the pressure is less than about 20 torr. In certain embodiments, the pressure is less than about 10 torr. In certain embodiments, the pressure is less than about 5 torr. In certain embodiments, the pressure is less than about 1 torr. In certain embodiments, the pressure is less than about 0.7 torr. In certain embodiments, the pressure is less than about 0.4 torr. In certain embodiments, the pressure is about 50 torr. In certain embodiments, the pressure is about 40 torr. In certain embodiments, the pressure is about 30 torr. In certain embodiments, the pressure is about 20 torr. In certain embodiments, the pressure is about 10 torr. In certain embodiments, the pressure is about 5 torr. In certain embodiments, the pressure is about 1 torr. In certain embodiments, the pressure is about 0.7 torr. In certain embodiments, the pressure is about 0.6 torr. In certain embodiments, the pressure is about 0.5 torr. In certain embodiments, the pressure is about 0.4 torr. In certain embodiments, the pressure is about 0.3 torr. In certain embodiments, the pressure is about 0.2 torr. In certain embodiments, the pressure is about 0.1 torr. In certain embodiments the pressure is about 1 torr; about 0.9 torr; about 0.8 torr; about 0.7 torr; about 0.6 torr; about 0.5 torr; about 0.4 torr; about 0.3 torr; about 0.2 torr; or about 0.1 torr.

In certain embodiments, the flow rate of the monomer can be adjusted in the CVD method. In certain embodiments, the monomer flow rate is about 100 sccm (standard cubic centimeters per minute). In certain embodiments, the monomer flow rate is about 90 sccm. In certain embodiments, the monomer flow rate is about 80 sccm. In certain embodiments the monomer flow rate is about 70 sccm. In certain embodiments, the monomer flow rate is about 60 sccm. In certain embodiments, the monomer flow rate is about 50 sccm. In certain embodiments, the monomer flow rate is about 40 sccm. In certain embodiments, the monomer flow rate is about 30 sccm. In certain embodiments, the monomer flow rate is about 20 sccm.

In certain embodiments, the monomer flow rate is less than about 100 sccm. In certain embodiments, the monomer flow rate is less than about 90 sccm. In certain embodiments, the monomer flow rate is less than about 80 sccm. In certain embodiments, the monomer flow rate is less than about 70 sccm. In certain embodiments, the monomer flow rate is less than about 60 sccm. In certain embodiments, the monomer flow rate is less than about 50 sccm. In certain embodiments, the monomer flow rate is less than about 40 sccm. In certain embodiments, the monomer flow rate is less than about 30 sccm. In certain embodiments, the monomer flow rate is less than about 20 sccm. In certain embodiments, the monomer flow rate is about 15 sccm. In certain embodiments, the flow rate is less than about 15 sccm. In certain embodiments, the monomer flow rate is about 14 sccm. In certain embodiments, the flow rate is less than about 14 sccm. In certain embodiments, the monomer flow rate is about 13 sccm. In certain embodiments, the flow rate is less than about 13 sccm. In certain embodiments, the monomer flow rate is about 12 sccm. In certain embodiments, the flow rate is less than about 12 sccm. In certain embodiments, the monomer flow rate is about 11 sccm. In certain embodiments, the flow rate is less than about 11 sccm. In certain embodiments, the monomer flow rate is about 10 sccm. In certain embodiments, the flow rate is less than about 10 sccm. In certain embodiments, the monomer flow rate is about 9 sccm. In certain embodiments, the flow rate is less than about 9 sccm. In certain embodiments, the monomer flow rate is about 8 sccm. In certain embodiments, the flow rate is less than about 8 sccm. In certain embodiments, the monomer flow rate is about 7 sccm. In certain embodiments, the flow rate is less than about 7 sccm. In certain embodiments, the monomer flow rate is about 6 sccm. In certain embodiments, the flow rate is less than about 6 sccm. In certain embodiments, the monomer flow rate is about 5 sccm. In certain embodiments, the flow rate is less than about 5 sccm. In certain embodiments, the monomer flow rate is about 3 sccm. In certain embodiments, the flow rate is less than about 3 sccm. In certain embodiments, the monomer flow rate is about 1.5 sccm. In certain embodiments, the flow rate is less than about 1.5 sccm. In certain embodiments, the monomer flow rate is about 0.75 sccm. In certain embodiments, the flow rate is less than about 0.75 sccm. In certain embodiments, the monomer flow rate is about 0.6 sccm. In certain embodiments, the flow rate is less than about 0.6 sccm. In certain embodiments, the monomer flow rate is about 0.5 sccm. In certain embodiments, the flow rate is less than about 0.5 sccm. When more than one monomer is used (i.e., to deposit co-polymers), the flow rate of the additional monomers, in certain embodiments, may be the same as those presented above.

In certain embodiments, the temperature of the monomer can be adjusted in the CVD method. In certain embodiments, the monomer can be heated and delivered to the chamber by a heated mass flow controller. In certain embodiments, the monomer can be heated and delivered to the chamber by a needle valve. In certain embodiments, the monomer is heated at about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

In certain embodiments, the flow rate of the initiator can be adjusted in the CVD method. In certain embodiments the initiator flow rate is from about 0.1 sccm to about 100 sccm. In certain embodiments the initiator flow rate is about 100 sccm. In certain embodiments, the initiator flow rate is about 90 sccm. In certain embodiments, the initiator flow rate is about 80 sccm. In certain embodiments, the initiator flow rate is about 70 sccm. In certain embodiments, the initiator flow rate is about 60 sccm. In certain embodiments, the initiator flow rate is about 50 sccm. In certain embodiments, the initiator flow rate is about 40 sccm. In certain embodiments, the initiator flow rate is about 30 sccm. In certain embodiments, the initiator flow rate is about 20 sccm. In certain embodiments, the initiator flow rate is less than about 100 sccm. In certain embodiments, the initiator flow rate is less than about 90 sccm. In certain embodiments, the initiator flow rate is less than about 80 sccm. In certain embodiments, the initiator flow rate is less than about 70 sccm. In certain embodiments, the initiator flow rate is less than about 60 sccm. In certain embodiments, the initiator flow rate is less than about 50 sccm. In certain embodiments, the initiator flow rate is less than about 40 sccm. In certain embodiments, the initiator flow rate is less than about 30 sccm. In certain embodiments, the initiator flow rate is less than about 20 sccm. In certain embodiments, the initiator flow rate is about 10 sccm. In certain embodiments, the flow rate is less than about 10 sccm. In certain embodiments, the initiator flow rate is about 5 sccm. In certain embodiments, the flow rate is less than about 5 sccm. In certain embodiments, the initiator flow rate is about 3 sccm. In certain embodiments, the flow rate is less than about 3 sccm. In certain embodiments, the initiator flow rate is about 1.5 sccm. In certain embodiments, the flow rate is less than about 1.5 sccm. In certain embodiments, the initiator flow rate is about 0.75 sccm. In certain embodiments, the flow rate is less than about 0.75 sccm. In certain embodiments, the initiator flow rate is about 0.5 sccm. In certain embodiments, the flow rate is less than about 0.5 sccm. In certain embodiments, the initiator flow rate is about 0.4 sccm. In certain embodiments, the flow rate is less than about 0.4 sccm. In certain embodiments, the initiator flow rate is about 0.3 sccm. In certain embodiments, the flow rate is less than about 0.3 sccm. In certain embodiments, the initiator flow rate is about 0.2 sccm. In certain embodiments, the flow rate is less than about 0.2 sccm. In certain embodiments, the initiator flow rate is about 0.1 sccm. In certain embodiments, the flow rate is less than about 0.1 sccm. In certain embodiments, a variety of initiators are useful in CVD; these initiators are well-known in the art.

In certain embodiments, the carrier gas is an inert gas. In certain embodiments, the carrier gas is nitrogen or argon.

In certain embodiments, the flow rate of the carrier gas can be adjusted in the CVD method. In certain embodiments, the carrier gas flow rate is about 1000 sccm. In certain embodiments, the carrier gas flow rate is about 900 sccm. In certain embodiments, the carrier gas flow rate is about 800 sccm. In certain embodiments, the carrier gas flow rate is about 700 sccm. In certain embodiments, the carrier gas flow rate is about 600 sccm. In certain embodiments, the carrier gas flow rate is about 500 sccm. In certain embodiments, the carrier gas flow rate is about 400 sccm. In certain embodiments, the carrier gas flow rate is about 300 sccm. In certain embodiments, the carrier gas flow rate is about 200 sccm. In certain embodiments, the carrier gas flow rate is about 100 sccm. In certain embodiments, the carrier gas flow rate is about 90 sccm. In certain embodiments, the carrier gas flow rate is about 80 sccm. In certain embodiments, the carrier gas flow rate is about 70 sccm. In certain embodiments, the carrier gas flow rate is about 60 sccm. In certain embodiments, the carrier gas flow rate is about 50 sccm. In certain embodiments, the carrier gas flow rate is about 40 sccm. In certain embodiments, the carrier gas flow rate is about 30 sccm. In certain embodiments, the carrier gas flow rate is about 20 sccm.

In certain embodiments, the carrier gas flow rate is less than about 1000 sccm. In certain embodiments, the carrier gas flow rate is less than about 900 sccm. In certain embodiments, the carrier gas flow rate is less than about 800 sccm. In certain embodiments, the carrier gas flow rate is less than about 700 sccm. In certain embodiments, the carrier gas flow rate is less than about 600 sccm. In certain embodiments, the carrier gas flow rate is less than about 500 sccm. In certain embodiments, the carrier gas flow rate is less than about 400 sccm. In certain embodiments, the carrier gas flow rate is less than about 300 sccm. In certain embodiments, the carrier gas flow rate is less than about 200 sccm. In certain embodiments, the carrier gas flow rate is less than about 100 sccm. In certain embodiments, the carrier gas flow rate is less than about 90 sccm. In certain embodiments, the carrier gas flow rate is less than about 80 sccm. In certain embodiments, the carrier gas flow rate is less than about 70 sccm. In certain embodiments, the carrier gas flow rate is less than about 60 sccm. In certain embodiments the carrier gas flow rate is less than about 50 sccm. In certain, embodiments the carrier gas flow rate is less than about 40 sccm. In certain embodiments, the carrier gas flow rate is less than about 30 sccm. In certain embodiments, the carrier gas flow rate is less than about 20 sccm. In certain embodiments, the carrier gas flow rate is about 10 sccm. In certain embodiments, the flow rate is less than about 10 sccm. In certain embodiments, the carrier gas flow rate is about 5 sccm. In certain embodiments, the flow rate is less than about 5 sccm. In certain embodiments, the carrier gas flow rate is about 4 sccm. In certain embodiments, the flow rate is less than about 4 sccm. In certain embodiments, the carrier gas flow rate is about 3 sccm. In certain embodiments, the flow rate is less than about 3 sccm. In certain embodiments, the carrier gas flow rate is about 2 sccm. In certain embodiments, the flow rate is less than about 2 sccm. In certain embodiments, the carrier gas flow rate is about 1 sccm. In certain embodiments, the flow rate is less than about 1 sccm.

In certain embodiments, the heating filament, radiation source, or the electrode is oriented in any orientation with respect to the substrate stage or the chamber. In certain embodiments, the filament is oriented above the substrate stage, below the substrate stage, or beside the substrate stage.

In certain embodiments, the CVD coating process can take place at a range of temperatures of the substrate stage. In certain embodiments, the temperature of the substrate stage is ambient temperature. In certain embodiments, the temperature is about −20 ° C. In certain embodiments, the temperature of the substrate is about −10 ° C. In certain embodiments, the temperature of the substrate is about 0 ° C. In certain embodiments, the temperature of the substrate stage is about 20 ° C.; in some embodiments, the substrate stage is about 30 ° C. In yet other embodiments the temperature of the substrate stage is between about 10 ° C. and about 100 ° C., or between about 0 ° C. and about 35 ° C. In certain embodiments said temperature of the substrate stage is controlled by water.

In certain embodiments, the rate of polymer deposition is about 1 micron/minute. In certain embodiments, the rate of polymer deposition is about 1 micron/minute to about 50 nm/minute. In certain embodiments, the rate of polymer deposition is about 10 micron/minute to about 50 nm/minute. In certain embodiments, the rate of polymer deposition is about 100 micron/minute to about 50 nm/minute. In certain embodiments, the rate of polymer deposition is about 1 nm/minute to about 50 nm/minute. In certain embodiments, the rate of polymer deposition is about 10 nm/minute to about 50 nm/minute. In certain embodiments, the rate of polymer deposition is about 10 nm/minute to about 25 nm/minute.

In some embodiments of the methods disclosed herein, the free radical initiator is selected from the group consisting of a peroxide, an aryl ketone, and an azo compound.

In some embodiments of the methods disclosed herein, the free radical initiator comprises triethylamine.

In some embodiments of the methods disclosed herein, the free radical initiator is an aryl ketone.

In some embodiments of the methods disclosed herein, the CVD is iCVD. In some embodiments, heating a free radical initiator produces a gaseous free radical initiator using thermal energy. In some embodiments, the free radical initiator is a peroxide or an azo compound. Examples of free radical initiators include, but are not limited to, 4,4'-Azobis (4-cyanovaleric acid), 1,1'-Azobis(cyclohexanecarbonitrile), 2,2'-Azobis(2-methylpropionamidine) dihydrochloride, and 2,2'-Azobis(2-methylpropionitrile). In some embodiments, the free radical initiator is 2,2'-Azobis(2-methylpropionitrile). In some embodiments, the free radical initiator is a peroxide selected from the group consisting of tert-butyl hydroperoxide, tent-butyl peracetate, cumene hydroperoxide, dicumyl peroxide, benzoyl peroxide, tent-amyl peroxide, tent-butyl peroxide, and tent-butyl peroxybenzoate. In some embodiments, the free radical initiator is tent-butyl peroxide.

In some embodiments of the methods disclosed herein, the CVD is piCVD. In some embodiments, irradiating a free radical initiator (e.g., using UV-light) produces a gaseous free radical initiator. Examples of photoinitiators include, but are not limited to, azobi si sobutyronitrile (AIBN), $H_2O_2$ (hydrogen peroxide), ethyl-2,4,6-trimethylbenzoylphenylphosphinate, 2,2'-azobis(2-methylpropane), benzophenone and its derivatives, and Michler's ketone. In one embodiment, the free radical initiator is an aryl ketone.

In some embodiments of the methods disclosed herein, the CVD is iPECVD. In some embodiments, irradiating a free radical initiator (e.g., using radiofrequency power or microwave power) produces a gaseous free radical initiator. Examples of free radical initiators include, but are not limited to tert-butyl peroxide, tert-amyl peroxide, triethylamine, tert-butylperoxy benzoate, benzophenone, and 2,2'-azobis (2-methylpropane) (ABMP).

In some embodiments of the methods disclosed herein, the monomer is at least one of an acrylate, an acrylamide, a siloxane, a silane, and a vinyl compound. In some embodiments, the monomer is a vinyl compound. In some embodiments, the monomer polymerizes quickly, e.g., is an acrylate. Example monomers include, but are not limited to, acrylates (e.g., methyl methacrylate, butyl acrylate, glycidyl methacrylate, hydroxyl ethyl methacrylate, ethylene glycol diacrylate, propargyl methacrylate, pentafluorophenyl methacrylate, hydroxyethyl methacrylate, cyclohexyl methacrylate, methacrylic acid-co-ethyl acrylate, acrylates with perfluoro side chains (e.g., 1H,1H,6H,6H-perfluorohexyldiacrylate, 1H,1H,2H,2H-perfluorooctyl acrylate, 1H,1H,2H,2H-perfluorodecyl acrylate)), N,N-dimethylacrylamide, polydimethylacrylamide, vinyl pyridine (e.g., 2-vinyl pyridine and 4-vinyl pyridine), divinylbenzene (e.g., p-divinylbenzene and m-divinylbenzene), trivinlytrimethylcyclotri siloxane, tetravinyltetramethylcyclotetrasiloxane, trichlorovinylsilane, di(ethylene glycol) divinyl ether, xylylene, vinylene, dimethylaminomethyl styrene, pyrrole, 3-thiopheneacetic acid, and copolymers thereof. In some embodiments, the monomer is selected from the group consisting of methyl methacrylate, butyl acrylate, glycidalmethacrylate, N,N-dimethylacrylamide, polydimethylacrylamide, vinyl pyridine, divinylbenzene, trivinlytrimethylcyclotrisiloxane, tetravinyltetramethylcyclotetra-siloxane, trichlorovinyl silane, di(ethylene glycol) divinyl ether, xylylene, and vinylene. In some embodiments, the monomer is N,N-dimethylacrylamide. In some embodiments, the monomer is polydimethylacrylamide. In some embodiments, the one or more monomers are N,N-dimethylacrylamide, polydimethylacrylamide, trichlorovinylsilane, and di(ethylene glycol) divinyl ether. In some embodiments, the one or more monomers are N,N-dimethylacrylamide, trichlorovinylsilane, and di(ethylene glycol) divinyl ether. In some embodiments, the one or more monomers are polydimethylacrylamide and di(ethylene glycol) divinyl ether.

Articles

In one aspect, provided herein is an article, comprising an object, a device, or an assembly, and a coating on a surface of an object, a device, or an assembly, wherein the coating comprises an ionic liquid, an ionic liquid complex, a neutral ethylene diamine, or a neutral ethylene diamine complex.

In another aspect, provided herein is a coated article comprising an object, a device, or an assembly and such a coating formed by any of the methods disclosed herein.

In some embodiments, for example, the article is selected from the group consisting of a conductive substrate (e.g., conductive strips, conductive sheets, or electrodes), filters (e.g., hand-held water filters), membranes (e.g., reverse osmosis membranes), tiles, packing materials (e.g., for foods, agriculture, paints, etc.), flow cells, filter gaskets, gloves, masks, garments, bed sheets, wound dressings, prosthetics, implants, catheters, and other medical devices, a medical tool, equipment, tubing, and a ship (e.g., a hull of a ship). In some embodiments, the article is selected from the group consisting of an electrode, a filter, a membrane, a tile, a packing material, a flow cell, a filter gasket, a medical tool, and a medical device. In some embodiments, the article is disposable or reusable. In some embodiments, the article comprises a flexible substrate. In some embodiments, the article comprises an inexpensive, flexible substrate.

In some embodiments, the article comprises a conductive substrate. In some embodiments, the conductive substrate is, for example, stainless steel, stainless steel foil, graphite, or glassy carbon. In some embodiments, the article is a conductive strip or a conductive sheet. In some embodiments, the conductive substrate is disposable or reusable. In some embodiments, the conductive substrate is reusable.

In some embodiments, the article comprises a substrate that is a component of an electrochemical cell. In some embodiments, the metal ions can be plated onto a conductive substrate by making the substrate with a polymer coating encapsulating ILs, IL complexes, neutral ethylene diamines, neutral ethylene diamine complexes and oils or polymer coatings comprising ILs, IL complexes, neutral ethylene diamines, or neutral ethylene diamine complexes into an electrode in an electrochemical cell.

In some embodiments, the article is, or is incorporated into, an electrochemical cell. In some embodiments, the electrochemical cell comprises:

(a) a coated substrate serving as a cathode;
(b) a counter electrode serving as an anode; and
(c) an electrolyte solution.

In some embodiments, the article is, for example, a medical tool, a medical device, equipment, or tubing. In some embodiments, the article is in contact with, for example, organs, tissue, fluids, or cells. In some embodiments, the article is a medical tool. In some embodiments, the article is a medical device. In some embodiments, the medical device is selected from the group consisting of a glove, a mask, a garment, a bed sheet, a wound dressing, a prosthetic, an implant, a catheter. In some embodiments, the medical device is a prosthetic, an implant, or a catheter. In some embodiments, the medical device is a catheter.

In some embodiments, the article is selected from the group consisting of a filter (e.g., a hand-held water filter), a membrane (e.g., a reverse osmosis membrane), a flow cell, and a filter gasket. In some embodiments, the article is a flow cell. In some embodiments, the article is, or is incorporated into, a water desalination device. In some embodiments, the article is, or is incorporated into, a filter. In some embodiments, the article is, or is incorporated into, a water filter. In some embodiments, the water filter comprises an electrochemical cell. In some embodiments, the article is a ship or a boat. In some embodiments, a surface of an object, a device, or an assembly is a hull of a ship, wherein said surface is exposed to water.

In some embodiments, the article is selected from the group consisting of a filter (e.g., a hand-held water filter), a membrane (e.g., a reverse osmosis membrane), a packing material (e.g., for foods, agriculture, paints, etc.), a flow cell, and a filter gasket. In some embodiments, the article is a packing material. In some embodiments, the packing material is for foods.

In some embodiments, the article is sterile.

In some embodiments of the methods disclosed herein, the article is reusable.

In some embodiments of the ionic liquids, ionic liquid complexes, neutral ethylene diamine compounds, neutral ethylene diamine complexes, and oils disclosed herein, the ionic liquids, ionic liquid complexes, neutral ethylene diamine compounds, neutral ethylene diamine complexes, and oils forms a microemulsion, an emulsion, or a gel.

Methods of Use
Antimicrobial Treatment

In another aspect, provided herein are methods of antimicrobial treatment using polymer coatings impregnated with ILs, IL complexes, and oils or polymer coatings comprising ILs, IL complexes, neutral ethylene diamines, and neutral ethylene diamine complexes. The ILs are highly tunable with effectively unlimited permutations (~$10^{18}$) available on the alkyl chain as well as through choice of anion. This controls both physicochemical properties such a solubility and melting point and also biological behavior. For example, it is well known that the longer alkyl chains (cationic surfactants) can have an additive effect to antibacterial properties [36] and this can be built into the IL design to enable synergistic antibacterial properties within the coatings. It is also known that Ag has enhanced antibacterial properties over Cu [37]. However, fungi are relatively more susceptible to copper toxicity than bacteria and blends of ILs and mixed metal systems within the coatings can be prepared for dual application.

Biofouling can occur when an article is in contact with biomaterial. In some embodiments, the disclosed methods of antimicrobial treatment reduce or prevent biofouling of an article, comprising an object, a device, or an assembly, and a coating on a surface of an object, a device, or an assembly, wherein the coating comprises an ionic liquid, an ionic liquid complex, a neutral ethylene diamine, a neutral ethylene diamine complex, or an oil. In some embodiments, the biomaterial is, for example, organs, tissue, fluids, or cells. In some embodiments, the organs, tissue, fluids, or cells are human organs, human tissue, human fluids, or human cells.

Biofouling can occur when an article is in contact with biomaterial for a period of time. In some embodiments, the period of time is from about one hour to several years. In some embodiments, the period of time is at least an hour. In some embodiments, the period of time is at least a day. In some embodiments, the period of time is at least a week. In some embodiments, the period of time is at least a month. In some embodiments, the period of time is at least three months. In some embodiments, the period of time is at least six months. In some embodiments, the period of time is at least nine months months. In some embodiments, the period of time is at least a year. In some embodiments, the period of time is from about one hour to about a month. In some embodiments, the period of time is from about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 21 hours, about 21.5 hours, about 22 hours, about 22.5 hours, about 23 hours, about 23.5 hours, about 1 day, about 1.5 days, about 2 days, about 2.5 days, about 3 days, about 3.5 days, about 4 days, about 4.5 days, about 5 days, about 5.5 days, about 6 days, about 6.5 days, about 7 days (1 week), about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, and about 1 month.

In some embodiments, provided herein is a method of antimicrobial treatment, comprising:
providing a sample comprising a plurality of microorganisms;
contacting the coating formed by any of the methods disclosed herein with the sample;
thereby killing or inhibiting the growth of at least a portion of the plurality of microorganisms in the sample.

In some embodiments, provided herein is a method of antimicrobial treatment, comprising:
providing a sample comprising a plurality of microorganisms, wherein said microorganisms comprise a metal cation;
contacting the coating formed by any of the methods disclosed herein with the sample;
thereby killing or inhibiting the growth of at least a portion of the plurality of microorganisms in the sample.

In some embodiments of the methods of antimicrobial treatment disclosed herein, at least a portion of the plurality of microorganisms is killed.

In some embodiments of the methods of antimicrobial treatment disclosed herein, the growth of at least a portion of the plurality of microorganisms is inhibited.

In some embodiments of the methods of antimicrobial treatment disclosed herein, the metal cation has a charge of +2. In some embodiments, the metal cation is a cation of Mg, Fe, Hg, Sr, Sn, Ca, Cd, Zn, Co, Cu, Pb, Ni, Sc, V, Cr, or Mn.

In some embodiments of the methods disclosed herein, the metal cation has a charge of +3. In some embodiments, the metal cation is a cation of Fe, La, Ce, Pr, Nd, Pm, Sm, Eu, Gd, Tb, Dy, Ho, Er, Tm, Yb, or Lu. In some embodiments, the metal cation is Fe(III).

In some embodiments of the methods disclosed herein, an ionic liquid complex comprising an ionic liquid chelated to a metal cation is formed.

In some embodiments, provided herein is a method of preventing or suppressing microbial growth on a surface, wherein the surface comprises a coating formed by any of the methods disclosed herein, thereby preventing or suppressing microbial growth on the surface.

In some embodiments of the methods of antimicrobial treatment disclosed herein, the sample further comprises water.

In still another aspect, disclosed herein are methods of antifouling using polymer coatings impregnated with ILs, oils, and IL complexes or polymer coatings comprising ILs and IL complexes.

In some embodiments, provided herein is a method of increasing biofouling resistance, comprising:

providing a sample comprising a plurality of microorganisms;

contacting the coating formed by any of the methods disclosed herein with the sample;

thereby killing or inhibiting the growth of at least a portion of the plurality of microorganisms in the sample.

In some embodiments, the microorganism is a bacterium, a virus, a fungus, or a parasite.

In some embodiments, the microorganism is a gram-negative bacterium. In some embodiments, the microorganism is a gram-positive bacterium. In some embodiments, for example, the microorganism is at least one bacterium selected from anthrax, *Bacilli*, *Bordetella*, *Borrelia*, botulism, *Brucella*, *Burkholderia*, *Campylobacter*, *Chlamydia*, cholera, *Clostridium*, *Conococcus*, *Corynebacterium*, diptheria, *Enterobacter*, *Enterococcus*, *Erwinia Escherichia*, *Francisella*, *Haemophilus*, *Heliobacter*, *Klebsiella*, *Legionella*, *Leptospira*, leptospirosis, *Listeria*, Lyme's disease, meningococcus, *Mycobacterium*, *Mycoplasma*, *Neisseria*, *Pasteurella*, *Pelobacter*, plague, *Pneumonococcus*, *Proteus*, *Pseudomonas*, *Rickettsia*, *Salmonella*, *Serratia*, *Shigella*, *Staphylococcus*, *Streptococcus*, tetanus, *Treponema*, *Vibrio*, *Yersinia* and *Xanthomonas*. In some embodiments, the microorganism is *Pseudomonas aeruginosa*.

In some mbodiments, for example, the microorganism is at least one virus selected from *Adenoviridae*, *Papillomaviridae*, *Polyomaviridae*, *Herpesviridae*, *Poxviridae*, *Hepadnaviridae*, *Parvoviridae*, *Astroviridae*, *Picornaviridae*, *Coronoviridae*, *Flaviviridae*, *Retroviridae*, *Thgaviridae*, *Arenaviridae*, *Bunyaviridae*, *Filoviridae*, *Orthomyxoviridae*, *Paramyxoviridae*, *Rhabdoviridae*, and *Reoviridae*. In certain embodiments, the virus may be arboviral encephalitis virus, adenovirus, herpes simplex type I, herpes simplex type 2, Varicella-zoster virus, Epstein-barr virus, cytomegalovirus, herpesvirus type 8, papillomavirus, BK. virus, coronavirus, echovirus, JC virus, smallpox, Hepatitis B, bocavirus, parvovirus B19, astrovirus, Norwalk virus, coxsackievirus, Hepatitis poliovirus, rhinovirus, severe acute respiratory syndrome virus, Hepatitis C, yellow fever, dengue virus, West Nile virus, rubella, Hepatitis E, human immunodeficiency virus (HIV), human T-cell lymphotropic virus (HTLV), influenza, guanarito virus, Junin virus, Lassa virus, Machupo virus, Sabia virus, Crimean-Congo hemorrhagic fever virus, ebola virus, Marburg virus, measles virus, molluscum virus, mumps virus, parainfluenza, respiratory syncytial virus, human metapneumovirus, Hendra virus, Nipah virus, rabies, Hepatitis D, rotavirus, orbivirus, coltivirus, vaccinia virus, and Banna virus.

In some embodiments, for example, the microorganism is at least one fungus selected from *Aspergillus* (*fumigatus*, *niger*, etc.), *Basidiobolus* (*ranarum*, etc), *Blastomyces dermatitidis*, *Candida* (*albicans*, *krusei*, *glabrata*, *tropicalis*, etc.), *Coccidioides immitis*, *Cryptococcus* (*neoformans*, etc.), eumycetoma, *Epidermophyton* (*floccosum*, etc), *Histoplasma capsulatum*, *Hortaea werneckii*, *Lacazia loboi*, *Microsproum* (*audouinii*, *namum* etc), *Mucorales* (*mucor*, *absidia*, *rhizophus*), *Paracoccidioides brasiliensis*, *Rhinosporidium seeberi*, *Sporothrix schenkii*, and *Trichophyton* (*schoeleinii*, *mentagrophytes*, *rubrum*, *verrucosum*, etc.).

In some embodiments, for example, the microorganism is at least one parasite selected from *Acanthamoeba*, *Babesia microti*, *Balantidium coli*, *Entamoeba hystolytica*, *Giardia lamblia*, *Coptosporidium muris*, *Trypanosomatida gambiense*, *Trypanosomatida rhodesiense*, *Trypanosoma brucei*, *Trypanosoma cruzi*, *Leishmania mexicana*, *Leishmania braziliensis*, *Leishmania tropica*, *Leishmania donovani*, *Toxoplasma gondii*, *Plasmodium vivax*, *Plasmodium ovate*, *Plasmodium malariae*, *Plasmodium falciparum*, *Pneumocystis carinii*, *Trichomonas vaginalis*, *Histomonas meleagridis*, *Secementea*, *Trichuris trichiura*, *Ascaris lumbricoides*, *Enterobius vermicularis*, *Ancylostoma duodenale*, *Naegleria fowleri*, *Necator americanus*, *Nippostrongylus brasiliensis*, *Strongyloides stercoralis*, *Wuchereria bancrofti*, *Dracunculus medinensis*, blood flukes, liver flukes, intestinal flukes, lung flukes, *Schistosoma mansoni*, *Schistosoma haematobium*, *Schistosoma japonicum*, *Fasciola hepatica*, *Fasciola gigantica*, *Heterophyes heterophyes*, and *Paragonimus westermani*.

In some embodiments, the ionogel coating is more effective at reducing or preventing microbial growth than alternatives (e.g., other coatings, other methods of coatings, and antibiotics).

In some embodiments, the cost of forming the ionogel coating is less than alternatives (e.g., antibiotics and metal coatings).

Metal Remediation

In yet another aspect, the present disclosure provides a method to extract metal ions from aqueous solution for water treatment using polymer coatings encapsulating ILs and oils or polymer coatings comprising ILs. In addition, the metal ions may be removed from polymer coatings encapsulating IL complexes and oils or polymer coatings comprising IL complexes, and the IL regenerated, by applying an electrochemical potential. In some embodiments, the regenerated IL can be used for further metal ion binding. In some embodiments, the IL complexes can become saturated by occupation of all of the chelation sites by metal ions. In some embodiments, the metal ions are metal cations. In some embodiments, the metal ions can be plated onto a conductive substrate.

In some embodiments, provided herein is a method of removing metal cations from an ionic liquid mixture, comprising:

providing a coating formed by any one of the methods disclosed herein comprising an ionic liquid mixture comprising an ionic liquid and a plurality of metal cations; and applying an electrical potential to the ionic liquid mixture, thereby removing from the ionic liquid mixture the plurality of metal cations.

In some embodiments of the methods of metal remediation provided herein, applying the electrical potential causes the plurality of metal cations to be electrochemically reduced.

In some embodiments of the methods of metal remediation provided herein, applying the electrical potential causes the plurality of metal cations to be electrochemically reduced to metal atoms.

In some embodiments, provided herein is a method of removing metal cations from an aqueous mixture, comprising:

providing an aqueous mixture comprising water and a plurality of metal cations; and contacting a coating formed by any of the methods disclosed herein comprising an ionic liquid with the aqueous mixture, thereby forming an ionic liquid mixture comprising the ionic liquid and the plurality of metal cations.

In some embodiments of the methods of metal remediation provided herein, the metal cations have a charge of +2. In some embodiments, the metal cations are cations of Mg, Fe, Hg, Sr, Sn, Ca, Cd, Zn, Co, Cu, Pb, Ni, Sc, V, Cr, Mn, or Ag. In some embodiments, the metal cations are cations of Ni, Zn, Cu, Pb, or Co.

Gas Absorption

In still another aspect, disclosed herein are methods of gas absorption using polymer coatings impregnated with ILs and IL complexes or polymer coatings comprising ILs and IL complexes.

In some embodiments, provided herein is a method of absorbing gasses, comprising:

providing a sample comprising a plurality of gasses;

contacting a coating formed by any of the methods disclosed herein with the sample;

thereby absorbing to the coating at least a portion of the plurality of gasses in the sample.

In some embodiments of the methods of gas absorption provided herein, the sample comprises a gas selected from the group consisting of $CO_2$, $SO_2$ and $H_2S$. In some embodiments, the gas is $H_2S$.

In some embodiments of the methods of gas absorption provided herein, the coating comprises a Michael acceptor.

In some embodiments of the methods of gas absorption provided herein, the coating comprises a Michael donor. In some embodiments, the coating comprises a nucleophile. In some embodiments, the nucleophile is an amine moiety (e.g., of structural formulas I, II, III, or IV).

Compounds of the Disclosure

Ionic Liquids

In some embodiments of the methods disclosed herein, the ionic liquid comprises a cation and an anion; and the cation is represented by the following structural formula I:

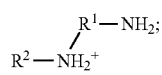
(I)

wherein, independently for each occurrence:
$R^1$ is —$(C(R)_2)_n$-;
n is 2, or 3;
$R^2$ is —$(C(R')_2)_m$-$R''$;
m is 1, 2, 3, 4, 5, 6, 7, 8, 9, or 10; and
R is H, F, $C_1$-$C_3$ alkyl, or $C_1$-$C_3$ fluoroalkyl;
R' is H, F, $C_1$-$C_8$ alkyl, or $C_1$-$C_8$ fluoroalkyl; and
R'' is H, F, $C_1$-$C_3$ alkyl, $C_1$-$C_3$ fluoroalkyl, $C_1$-$C_3$ alkyloxy, $C_1$-$C_3$ fluoroalkyloxy, $C_6$-$C_{10}$ aryl, $C_2$-$C_8$ alkenyl or $C_2$-$C_8$ fluoroalkenyl; wherein each instance of $C_6$-$C_{10}$ aryl is optionally substituted with one, two, three, four or five substituents independently selected from the group consisting of F, $C_1$-$C_3$ alkyl, $C_1$-$C_3$ fluoroalkyl, $C_1$-$C_3$ alkyloxy, and $C_1$-$C_3$ fluoroalkyloxy.

The variables in formula I may be further selected as described below.

In some embodiments of the methods disclosed herein, the ionic liquid comprises a cation and an anion; and the cation is represented by the following structural formula II:

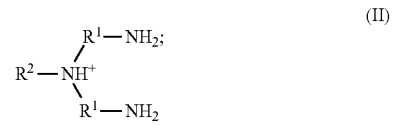
(II)

wherein, independently for each occurrence:
$R^1$ is —$(C(R)_2)_n$-;
n is 2, or 3;
$R^2$ is —$(C(R')_2)_m$-$R''$;
m is 1, 2, 3, 4, 5, 6, 7, 8, 9, or 10; and
R is H, F, $C_1$-$C_3$ alkyl, or $C_1$-$C_3$ fluoroalkyl;
R' is H, F, $C_1$-$C_8$ alkyl, or $C_1$-$C_8$ fluoroalkyl; and
R'' is H, F, $C_1$-$C_3$ alkyl, $C_1$-$C_3$ fluoroalkyl, $C_1$-$C_3$ alkyloxy, $C_1$-$C_3$ fluoroalkyloxy, $C_6$-$C_{10}$ aryl, $C_2$-$C_8$ alkenyl or $C_2$-$C_8$ fluoroalkenyl; wherein each instance of $C_6$-$C_{10}$ aryl is optionally substituted with one, two, three, four or five substituents independently selected from the group consisting of F, $C_1$-$C_3$ alkyl, $C_1$-$C_3$ fluoroalkyl, $C_1$-$C_3$ alkyloxy, and $C_1$-$C_3$ fluoroalkyloxy.

The variables in formula II may be further selected as described below.

In some embodiments of the ionic liquids disclosed herein, the anion is boron tetrafluoride, phosphorus tetrafluoride, phosphorus hexafluoride, alkylsulfonate, fluoroalkylsulfonate, aryl sulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin. In some embodiments, the anion is boron tetrafluoride, phosphorus tetrafluoride, phosphorus hexafluoride, halide, nitrate, nitrite, sulfate, hydrogensulfate, carbonate, bicarbonate, phosphate, hydrogen phosphate, dihydrogen phosphate, hypochlorite, or an anionic site of a cation-exchange resin. In some embodiments, the anion is $C_1$-$C_{12}$ alkyl sulfonate, $C_1$-$C_{12}$ fluoroalkylsulfonate, $C_6$-$C_{10}$ aryl sulfonate, $C_2$-$C_{24}$ bis(alkylsulfonyl)amide, $C_2$-$C_{24}$ bis(fluoroalkylsulfonyl)amide, $C_{12}$-$C_{20}$ bis(arylsulfonyl)amide, $C_2$-$C_{24}$ (fluoroalkylsulfonyl)(fluoroalkylcarbonyl)amide, $C_1$-$C_{12}$ alkyl sulfate, $C_6$-$C_{10}$ aryl sulfate, or $C_1$-$C_{12}$ carboxylate. In some embodiments, the anion is boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide. In some embodiments, the anion is methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide. In some embodiments, the anion is bis(methanesulfonyl)amide, bis(trifluoromethanesulfonyl)amide, bis(benzenesulfonyl)amide, or bis(p-toluenesulfonyl)amide. In some embodiments, the anion is bis(trifluoromethanesulfonyl)amide or (trifluoromethanesulfonyl)(trifluoroacetyl)amide. In some embodiments, the anion is bis(trifluoroethanesulfonyl)amide.

In some embodiments of the ionic liquids disclosed herein, the anion is antimicrobial. For example, the antimicrobial anion is penicillin or a related carboxylic acid (e.g., ampicillin, carbenicillin, oxacillin, narcillin, and cloxacillin). In some embodiments, the antimicrobial anion is ampicillin.

Figure 5:
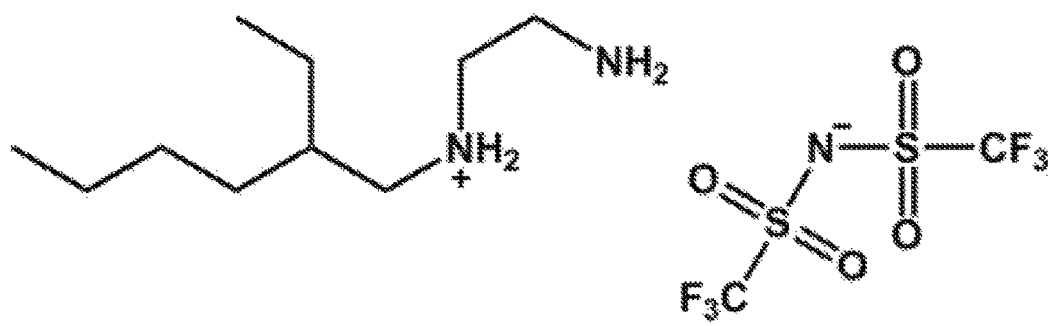
FIG. 5 shows the structure of ionic liquid [eth-hex-en][Tf$_2$N].

In some embodiments, the ionic liquid is [HHex][Tf$_2$N] (FIG. 1). In some embodiments, the ionic liquid is [eth-hexen][Tf$_2$N] (FIG. 5).

In some embodiments, the ionic liquid comprises poly(diallyldimethylammonium) cations and ampicillin counterions.

In some embodiments of the methods disclosed herein, the ionic liquid comprises hydropobic moieties. In some embodiments, the hydrophobic moieties comprise one or more fluorinated moieties.

The physicochemical properties (e.g., viscosity) of the ionic liquids disclosed herein can be adjusted based on the chemical structure. In some embodiments of the methods disclosed herein, the ionic liquid, the oil, or mixtures comprising the ionic liquid or the oil has a low viscosity so as not to impede flow of a sample through the system. In some embodiments, the viscosity of the ionic liquid, the oil, or mixtures comprising the ionic liquid or the oil is less than 1 Pa s (1000 cP).

In some embodiments of the methods disclosed herein, the ionic liquid has a high selectivity for transition metal ions (e.g., Fe, Hg, Cd, Zn, Co, Cu, Ni, Sc, V, Cr, and Mn). For example, the ionic liquid has a removal efficiency of at least 75%, at least 80%, at least 85%, at least 90%, at least 95%, at least 96%, at least 97%, at least 98%, or at least 99%.

Ionic Liquid Complexes and Neutral Ethylene Diamine Complexes

In some embodiments of the methods disclosed herein, wherein an ionic liquid complex comprising an ionic liquid chelated to a metal cation is formed or a neutral ethylene diamine complex, comprising a neutral ethylene diamine compound and a metal cation chelated by the neutral ethylene diamine is formed, the ionic liquid complex or the neutral ethylene diamine complex does not precipitate out of an aqueous solution. This is an improvement over other known ionic liquid complexes that precipitate out of aqueous solution, which can interfere with flow of a sample through the system.

In some embodiments of the methods disclosed herein, provided herein is an ionic liquid complex, comprising an ionic liquid chelated to a metal cation, wherein the ionic liquid comprises a cation and an anion; and the cation is represented by structural formula I as described above and below.

In some embodiments of the methods disclosed herein, provided herein is an ionic liquid complex, comprising an ionic liquid chelated to a metal cation, wherein the ionic liquid comprises a cation and an anion; and the cation is represented by structural formula II as described above and below.

In some embodiments of the methods disclosed herein, provided herein is a neutral ethylene diamine complex, comprising a metal cation chelated by the neutral ethylene diamine compound, wherein the neutral ethylene diamine compound is represented by structural formula III as described above and below.

In some embodiments of the methods disclosed herein, provided herein is a neutral ethylene diamine complex, comprising a metal cation chelated by the neutral ethylene diamine compound, wherein the neutral ethylene diamine compound is represented by structural formula IV as described above and below.

In some embodiments of the complexes described herein, the metal cation has a charge of +1. In some embodiments, the metal cation is a cation of Ag.

In some embodiments of the complexes described herein, the metal cation is a cation of Ca, Cu, or Zn. In some embodiments, the metal cation is a cation of Cu.

Polymers

In some embodiments of the methods disclosed herein, the polymer-coated surface comprises a copolymer. In some embodiments, a cross-linked coating is formed from a mixture comprising a first gaseous monomer selected from the group consisting of an acrylate, an acrylamide, an alkene, a silane, and a siloxane compound and a second gaseous monomer, wherein the second gaseous monomer comprises an ionic liquid.

In some embodiments, the ionic liquid comprises a metal-chelating group. In some embodiments, the metal-chelating group is selected from the group consisting of an ethylaminediacetic acid moiety, a crown ether, a dithizone, a hydroxyl-quinoline, 2-thenoyltrifluoroacetone, a thiosalicylate, a salicylate, a thiocarbamate, and an alkanolamine.

In some embodiments, the ionic liquid comprises a cation and an anion. In some embodiments, the cation is represented by the following structural formula I:

(I)

wherein, independently for each occurrence:
R$^1$ is —(C(R)$_2$)$_n$—;
n is 2, or 3;
R$^2$ is —(C(R')$_2$)$_m$-R";
m is 1, 2, 3, 4, 5, 6, 7, 8, 9, or 10; and
R is H, F, C$_1$-C$_3$ alkyl, or C$_1$-C$_3$ fluoroalkyl;
R' is H, F, C$_1$-C$_8$ alkyl, or C$_1$-C$_8$ fluoroalkyl; and
R" is C$_6$-C$_{10}$ aryl, C$_2$-C$_8$ alkenyl or C$_2$-C$_8$ fluoroalkenyl; wherein each instance of C$_6$-C$_{10}$ aryl is substituted with one, two, three, four or five substituents independently selected from the group consisting of C$_2$-C$_8$ alkenyl or C$_2$-C$_8$ fluoroalkenyl.

In some embodiments, the cation is represented by the following structural formula II:

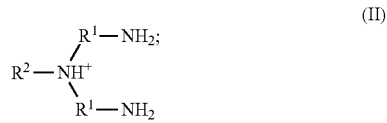

(II)

wherein, independently for each occurrence:
R$^1$ is —(C(R)$_2$)$_n$—;
n is 2, or 3;
R$^2$ is —(C(R')$_2$)$_m$-R";
m is 1, 2, 3, 4, 5, 6, 7, 8, 9, or 10; and
R is H, F, C$_1$-C$_3$ alkyl, or C$_1$-C$_3$ fluoroalkyl;
R' is H, F, C$_1$-C$_8$ alkyl, or C$_1$-C$_8$ fluoroalkyl; and
R" is C$_6$-C$_{10}$ aryl, C$_2$-C$_8$ alkenyl or C$_2$-C$_8$ fluoroalkenyl; wherein each instance of C$_6$-C$_{10}$ aryl is substituted with one, two, three, four or five substituents independently selected from the group consisting of C$_2$-C$_8$ alkenyl or C$_2$-C$_8$ fluoroalkenyl.

In some embodiments, a cross-linked coating is formed from a mixture comprising a first gaseous monomer selected from the group consisting of an acrylate, an acrylamide, an alkene, a silane, and a siloxane compound and a second gaseous monomer, wherein the second gaseous monomer comprises an ionic liquid complex, wherein the ionic liquid complex comprises an ionic liquid chelated to a metal cation, wherein the ionic liquid comprises a cation and an anion. In some embodiments, the cation is represented by structural formulas I or II of this section.

The variables in formulas I and II may be further selected as described above and below.

In some embodiments, a cross-linked coating is formed from a mixture comprising a first gaseous monomer selected from the group consisting of an acrylate, an acrylamide, an alkene, a silane, and a siloxane compound and a second gaseous monomer, wherein the second gaseous monomer comprises a neutral ethylene diamine compound represented by the following structural formula III:

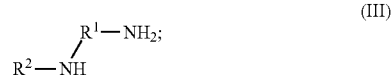

(III)

wherein, independently for each occurrence:
$R^1$ is —$(C(R)_2)_n$-;
n is 2, or 3;
$R^2$ is —$(C(R')_2)_m$-R";
m is 1, 2, 3, 4, 5, 6, 7, 8, 9, or 10; and
R is H, F, $C_1$-$C_3$ alkyl, or $C_1$-$C_3$ fluoroalkyl;
R' is H, F, $C_1$-$C_8$ alkyl, or $C_1$-$C_8$ fluoroalkyl; and
R" is $C_6$-$C_{10}$ aryl, $C_2$-$C_8$ alkenyl or $C_2$-$C_8$ fluoroalkenyl;
wherein each instance of $C_6$-$C_{10}$ aryl is substituted with one, two, three, four or five substituents independently selected from the group consisting of $C_2$-$C_8$ alkenyl or $C_2$-$C_8$ fluoroalkenyl.

In some embodiments, a cross-linked coating is formed from a mixture comprising a first gaseous monomer selected from the group consisting of an acrylate, an acrylamide, an alkene, a silane, and a siloxane compound and a second gaseous monomer, wherein the second gaseous monomer comprises a neutral ethylene diamine compound represented by the following structural formula IV:

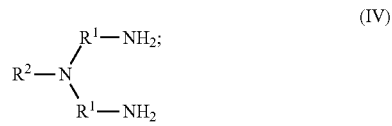

(IV)

wherein, independently for each occurrence:
$R^1$ is —$(C(R)_2)_n$-;
n is 2, or 3;
$R^2$ is —$(C(R')_2)_m$-R";
m is 1, 2, 3, 4, 5, 6, 7, 8, 9, or 10; and
R is H, F, $C_1$-$C_3$ alkyl, or $C_1$-$C_3$ fluoroalkyl;
R' is H, F, $C_1$-$C_8$ alkyl, or $C_1$-$C_8$ fluoroalkyl; and
R" is $C_6$-$C_{10}$ aryl, $C_2$-$C_8$ alkenyl or $C_2$-$C_8$ fluoroalkenyl;
wherein each instance of $C_6$-$C_{10}$ aryl is substituted with one, two, three, four or five substituents independently selected from the group consisting of $C_2$-$C_8$ alkenyl or $C_2$-$C_8$ fluoroalkenyl.

The variables in formulas III and IV may be further selected as described above and below.

In some embodiments, a neutral ethylene diamine complex is formed, further comprising a metal cation chelated by the neutral ethylene diamine. In some embodiments of the methods disclosed herein, the second monomer comprises a neutral ethylene diamine complex, comprising a neutral ethylene diamine compound chelated to a metal cation. In some embodiments, the neutral ethylene diamine is represented by structural formulas III or IV. In some embodiments, the neutral ethylene diamine is N-(4-vinyl)benzyl-ethylene-diamine (VBEDA).

In some embodiments, the polymers comprise VBEDA monomers as a second monomer. The VBEDA monomer has been synthesized previously [38, 39], but antimicrobial properties have not been reported. In addition the structure of the EDA group previously was not altered to convert to an ionic liquid monomer (polyelectrolyte product). Antimicrobial properties of polymers with pendant biguanide groups has been demonstrated [40]. A wide variety of copolymers may be utilized to obtain the required physicochemical properties. Sakohara et al. [39] used N-isopropylacrylamide (NIPAM) as the co-monomer to create thermoresponsive gels with a lower critical solution temperature (LCST) but other groups could be used to affect solubility on a range of solvents or combine with cationic monomers (with surfactant properties) for potential synergistic effects. Such polymers have advantages over small molecule antimicrobial agents as they demonstrate greater ability to disrupt the cell wall, bind to the bacterial membrane and adsorb to the surface. Polymeric cations may also be combined with antimicrobial anions. For example, cationic polymers based on poly(diallyldimethylammonium) cations with ampicillin counterions. Ampicillin is a known antimicrobial agent. Metal containing polymers with antimicrobial activity (polymeric biocides) have not been investigated before.

In some embodiments, the molar ratio of the first monomer to the second monomer is 100:1 to 1:1.

In some embodiments, the first monomer is present at about 90 mol % to about 99 mol % while the second monomer is present at about 1 mol % to about 10 mole %. In some embodiments, the first monomer is present at about 95 mol % while the second monomer is present at about 5 mol %.

In some embodiments of the methods disclosed herein, a metal cation is chelated to the cross-linked coating after the cross-linked coating is formed. In some embodiments, the molar ratio of the second monomer to the metal cation about 1:1. In some embodiments, the molar ratio of the second monomer comprising an IL to the metal cation about 1:1. In some embodiments, the molar ratio of the second monomer comprising a neutral ethylene diamine compound to the metal cation about 1:1. In some embodiments, the metal content varies from about 5 mol % to about 40 mol %.

In some embodiments of methods disclosed herein, the cross-linked coatings are hydrophobic. In some embodiments, the cross-linked coatings are fluorinated. In some embodiments, the cross-linked coatings are water insoluble.

In some embodiments of the methods disclosed herein, the neutral ethylene diamine is converted to an ionic liquid monomer before the coating is formed. In some embodiments, the cross-linked coating comprising a neutral ethylene diamine is converted to an ionic liquid after the coating is formed.

In some embodiments of the methods disclosed herein, the first monomer is an acrylamide. In some embodiments, the first monomer is N,N-dimethylacrylamide. In some embodiments, the first monomer is polydimethylacrylamide.

Exemplary Embodiments of Variables in Structural Formulas I, II, III, and IV

In some embodiments of structural formula I, II, III, or IV, n is 3. In some embodiments, n is 2. The remainder of the variables in structural formulas I, II, III, or IV may be selected as described above or below.

In some embodiments of structural formula I, II, III, or IV, m is 1, 2, 3, or 4. In some embodiments, m is 5, 6, or 7. In some embodiments, m is 8, 9, or 10. In some embodiments, m is 1. In some embodiments, m is 4. In some embodiments, m is 6. The remainder of the variables in structural formulas I, II, III, or IV may be selected as described above or below.

In some embodiments of structural formula I, II, III, or IV, R is F. In some embodiments, R is, for each instance independently, $C_1$-$C_3$ alkyl. In some embodiments, R is, for each instance independently, $C_1$-$C_3$ fluoroalkyl. In some embodiments, R is H. The remainder of the variables in structural formulas I, II, III, or IV may be selected as described above or below.

In some embodiments of structural formula I, II, III, or IV, R' is F. In some embodiments, R' is $C_1$-$C_8$ alkyl. In some embodiments, R' is $C_1$-$C_8$ fluoroalkyl. In some embodiments, R' is H. The remainder of the variables in structural formulas I, II, III, or IV may be selected as described above or below.

In some embodiments of structural formula I, II, III, or IV, R" is F. In some embodiments, R" is $C_1$-$C_3$ alkyl. In some embodiments, R" is $C_1$-$C_3$ fluoroalkyl. In some embodiments, R" is $C_1$-$C_3$ alkyloxy. In some embodiments, R" is $C_1$-$C_3$ fluoroalkyloxy. In some embodiments, R" is $C_6$-$C_{10}$ aryl. In some embodiments, R" is $C_2$-$C_8$ alkenyl. In some embodiments, R" is $C_2$ alkenyl. In some embodiments, R" is $C_2$-$C_8$ fluoroalkenyl. In some embodiments, R" is H.

In some embodiments, R" is $C_6$-$C_{10}$ aryl, $C_2$-$C_8$ alkenyl or $C_2$-$C_8$ fluoroalkenyl;
wherein each instance of $C_6$-$C_{10}$ aryl is substituted with one, two, three, four or five substituents independently selected from the group consisting of $C_2$-$C_8$ alkenyl or $C_2$-$C_8$ fluoroalkenyl.

In some embodiments, when R" is $C_6$-$C_{10}$ aryl, it is unsubstituted.

In some embodiments, when R" is $C_6$-$C_{10}$ aryl, it is substituted. In some embodiments, when R" is $C_6$ aryl, it is substituted.

In some embodiments, the one or more substituents on R" are independently selected from F, $C_1$-$C_3$ alkyl, and $C_1$-$C_3$ fluoroalkyl. In some embodiments, the one or more substituents on R" are independently selected from $C_1$-$C_3$ alkyl. In some embodiments, the one or more substituents on R" are independently selected from $C_2$-$C_8$ alkenyl or $C_2$-$C_8$ fluoroalkenyl. In some embodiments, the one or more substituents on R" are independently selected from $C_2$-$C_8$ alkenyl. In some embodiments, the one or more substituents on R" are independently $C_2$ alkenyl. In some such embodiments, R" is substituted with one substituent selected from the group consisting of F, $C_1$-$C_3$ alkyl, $C_1$-$C_3$ fluoroalkyl, $C_1$-$C_3$ alkyloxy, and $C_1$-$C_3$ fluoroalkyloxy. In some such embodiments, R" is substituted with two substituents selected from the group consisting of F, $C_1$-$C_3$ alkyl, $C_1$-$C_3$ fluoroalkyl, $C_1$-$C_3$ alkyloxy, and $C_1$-$C_3$ fluoroalkyloxy. In some such embodiments, R" is substituted with three such substituents. In some such embodiments, R" is substituted with four such substituents. In some such embodiments, R" is substituted with five such substituents. The remainder of the variables in structural formulas I, II, III, or IV may be selected as described above or below.

In some embodiments of structural formula I, II, III, or IV, n is 2; and R is H. In some embodiments, m is 1; R" is substituted $C_6$ aryl, wherein the substituent on R" is $C_2$ alkenyl. The remainder of the variables in structural formulas I, II, III, or IV may be selected as described above or below.

In some embodiments of structural formula I or II, m is 4; and R" is H. In some embodiments, $R^2$ is butyl. In some embodiments, m is 6; and R" is H.

In some embodiments, $R^2$ is 2-ethylhexyl. In some embodiments, $R^2$ is hexyl. The remainder of the variables in structural formulas I or II may be selected as described above or below.

Definitions

Unless otherwise defined herein, scientific and technical terms used in this application shall have the meanings that are commonly understood by those of ordinary skill in the art. Generally, nomenclature used in connection with, and techniques of, chemistry described herein, are those well-known and commonly used in the art.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Typically, a straight chained or branched alkenyl group has from 1 to about 20 carbon atoms, preferably from 1 to about 10 unless otherwise defined. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. In some embodiments, the alkyl group has from 1 to 8 carbon atoms, from 1 to 6 carbon atoms, from 1 to 4 carbon atoms, or from 1 to 3 carbon atoms. Examples of straight chained and branched alkyl groups include methyl, ethyl, n-propyl, iso-propyl, n-butyl, sec-butyl, tert-butyl, pentyl, hexyl, pentyl and octyl.

Moreover, the term "alkyl" as used throughout the specification, examples, and claims is intended to include both "unsubstituted alkyls" and "substituted alkyls", the latter of which refers to alkyl moieties having substituents replacing a hydrogen on one or more substitutable carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "arylthio", as used herein, refers to a thiol group substituted with an alkyl group and may be represented by the general formula arylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Typically, a straight chained or branched alkynyl group has from 1 to about 20 carbon atoms, preferably from 1 to about 10 unless otherwise defined. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

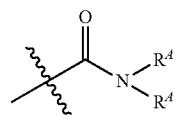

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

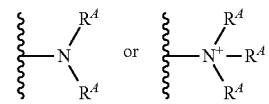

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 20-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

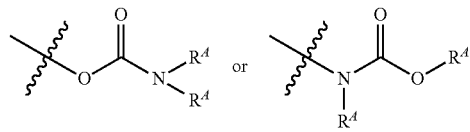

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. Preferably, a carbocylic group has from 3 to 20 carbon atoms. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings.

Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be susbstituted at any one or more positions capable of bearing a hydrogen atom.

A "cycloalkyl" group is a cyclic hydrocarbon which is completely saturated. "Cycloalkyl" includes monocyclic and bicyclic rings. Preferably, a cycloalkyl group has from 3 to 20 carbon atoms. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate", as used herein, refers to a group —$OCO_2$-$R^A$, wherein $R^A$ represents a hydrocarbyl group.

The term "carboxy", as used herein, refers to a group represented by the formula —$CO_2H$.

The term "ester", as used herein, refers to a group —$C(O)OR^A$ wherein $R^A$ represents a hydrocarbyl group.

The term "ether", as used herein, refers to a hydrocarbyl group linked through an oxygen to another hydrocarbyl group. Accordingly, an ether sub stituent of a hydrocarbyl group may be hydrocarbyl-O-. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 20-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 20-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom, wherein that carbon atom does not have a =O or =S substituent. Hydrocarbyls may optionally include heteroatoms. Hydrocarbyl groups include, but are not limited to, alkyl, alkenyl, alkynyl, alkoxyalkyl, aminoalkyl, aralkyl, aryl, aralkyl, carbocyclyl, cycloalkyl, carbocyclylalkyl, heteroaralkyl, heteroaryl groups bonded through a carbon atom, heterocyclyl groups bonded through a carbon atom, heterocyclylakyl, or hydroxyalkyl. Thus, groups like methyl, ethoxyethyl, 2-pyridyl, and trifluoromethyl are hydrocarbyl groups, but substituents such as acetyl (which has a =O substituent on the linking carbon) and ethoxy (which is linked through oxygen, not carbon) are not.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are six or fewer non-hydrogen atoms in the substituent. A "lower alkyl", for example, refers to an alkyl group that contains six or fewer carbon atoms. In some embodiments, the alkyl group has from 1 to 6 carbon atoms, from 1 to 4 carbon atoms, or from 1 to 3 carbon atoms. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

In the phrase "poly(meta-phenylene oxides)", the term "phenylene" refers inclusively to 6-membered aryl or 6-membered heteroaryl moieties. Exemplary poly(meta-phenylene oxides) are described in the first through twentieth aspects of the present disclosure.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Moieties that may be substituted can include any appropriate substituents described herein, for example, acyl, acylamino, acyloxy, alkoxy, alkoxyalkyl, alkenyl, alkyl, alkylamino, alkylthio, arylthio, alkynyl, amide, amino, aminoalkyl, aralkyl, carbamate, carbocyclyl, cycloalkyl, carbocyclylalkyl, carbonate, ester, ether, heteroaralkyl, heterocyclyl, heterocyclylalkyl, hydrocarbyl, silyl, sulfone, or thioether. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfonate" is art-recognized and refers to the group $SO_3H$, or a pharmaceutically acceptable salt thereof.

The term "sulfone" is art-recognized and refers to the group $—S(O)_2$-$R^A$, wherein $R^A$ represents a hydrocarbyl.

The term "thioether", as used herein, is equivalent to an ether, wherein the oxygen is replaced with a sulfur.

The phrase "chemical vapor deposition" (CVD), as used herein, refers to a powerful technology to provide polymeric coatings to be deposited without solvents. Already there are many examples of where CVD is employed in marketplace products such as medical devices, lubricious surfaces on industrial parts and printed circuit boards. In CVD polymerization, gas phase monomers are converted directly to thin solid macromolecular films. By eliminating the need to dissolve macromolecules, CVD allows the synthesis of insoluble polymers and highly crosslinked organic networks. Importantly, these CVD polymer films can be applied to nearly any substrate, and in some cases is the only fabrication option. Film thickness is achievable in the range 10 nm-200 µm. The use of an initiator not only allows the chemistry to be controlled, but also accelerates film growth and provides molecular-weight and rate control. The energy input is low due, but high growth rates may be achieved. The process progresses independent from the shape or composition of the substrate, is easily scalable, and easily integrated with other processes. The abbreviation "iCVD" is used for initiated chemical vapor deposition. In an iCVD process, thin filament wires are heated, thus supplying the energy to fragment a thermally-labile initiator, thereby forming a radical at moderate temperatures. The energy input is low due to the low filament temperatures.

The abbreviation "piCVD" is used for photoinitiated chemical vapor deposition. In a piCVD process, irradiating a free radical initiator (e.g., using UV-light) produces a gaseous free radical initiator.

The abbreviation "iPECVD" is used for initiated plasma-enhanced chemical vapor deposition. In an iPECVD process, applying low plasma power to an initiator with weak bonds produces a gaseous free radical initiator. For example, the low plasma power can be produced by a radiofrequency-induced glow discharge. The plasma can be produced by an electrode such as a microwave frequency electrode, a DC electrode, or a radiofrequency electrode.

The term "ionic liquids" (ILs), as used herein, refers salts with a melting point below 100° C. and that are liquid at room temperature. ILs have been used as highly customizable solvents for almost any synthetic purpose.

The phrase "task specific ionic liquids", as used herein, are ionic liquids with specific functionality that goes beyond simply being employed as a solvent. For example, tasks include, but are not limited to, catalysis, gas absorption, metal recovery for environmental remediation, and killing microbes such as bacteria.

The term "ionogels", as used herein, are analogous to hydrogels (interpenetrating networks of polymer chains and water) except that now the water is substituted for a non-evaporating liquid, an ionic liquid or an IL complex. That is, interpenetrating networks of polymer chains and ILs or IL complexes.

EXAMPLES

The invention now being generally described, it will be more readily understood by reference to the following examples, which are included merely for purposes of illustration of certain aspects and embodiments of the present invention, and are not intended to limit the invention.

Example 1

Synthesis of N-hexylethylenediaminium bis(trifluoroethanesulfonyl)amide, [Hhex][$Tf_2N$]

N-hexylethylenediaminium bis(trifluoroethanesulfonyl) amide, [HHex][$Tf_2N$] (FIG. 1), was synthesized according to the following procedure.

Bis(trifluoromethane)sulfonamide ($Tf_2NH$)>95%) and [HHex][$Tf_2N$] were purchased from Santa Cruz Biotechnology, 1-bromohexane (98%), ethylenediamine (>99%), copper (II) nitrate trihydrate (puriss) were purchased from Sigma Aldrich and used without further purification.

Hexyl(ethylenediamine) was synthesized by adding 1-bromohexane (35 mL, 0.25 moles) dropwise to an excess of ethylenediamine (250 mL, 3.75 moles) over 2 hours. After the reaction mixture was stirred overnight the unreacted ethylenediamine was removed at reduced pressure. The residue was washed with 40% sodium hydroxide solution, the top layer was removed and further washed with water. The product was then purified by distillation under reduced pressure (90° C., ~10 mbar).

Hexyl(ethylenediamine) was neutralized with acid ($Tf_2NH$) by mixing in 1:1 molar ratio in diethyl ether solution and then isolated by evaporation of the diethyl ether. The compound was dried in vacuo until the water content fell below 500 ppm (as measured by Karl Fischer titration). Purity of the compounds was confirmed by elemental analysis and $^1$H-NMR peaks agreed with the literature. The ionic liquid had a melting point of about −100° C. N-butyl(ethylenediaminium) bis(trifluoroethanesulfonyl)amide was prepared similarly.

Example 2

Polymer Formation by Chemical Vapor Deposition

Figure 2:
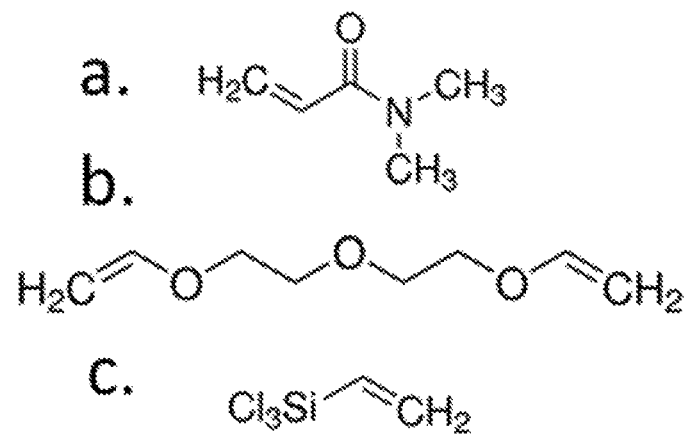
FIG. 2 shows an exemplary set of compounds used to create a CVD polymer film on a flow cell surface. (a) N,N-dimethylacrylamide; (b) the crosslinker was di(ethylene glycol) divinyl ether; (c) and the grafting agent trichlorovinylsilane.

Chemical vapor deposition (CVD) was used to cross-link a polymer and bind it to a flow cell surface using in a custom built vacuum reactor (Sharon Vacuum) previously described (Martin, T. P. et al. *Biomaterials* 2007, 28, 909-915; and Ozaydin-Ince, G. et al. *J. Vac. Sci. Technol., A* 2009, 27, 1135-1143). During CVD depositions, tert-butyl peroxide (TBPO) and monomers N,N-dimethylacrylamide (DMIVIA, FIG. 2A) and di(ethylene glycol) divinyl ether (DEGDVE, FIG. 2B) were introduced into the CVD reactor through mass flow controllers (1479 MFC, MKS Instruments). The grafting agent was trichlorovinylsilane (FIG. 2C), which covalently grafted the polymer network onto the surface via silanization. DMMA, which was the repeating unit in the polymer chains, was introduced into the chamber at a rate of about 2.8 mL/min. The crosslinker DEGDVE, which linked different polymer chains, was introduced into the chamber at a rate of 0.3 mL/min. The initiator TBPO was introduced into the chamber at a rate of about 1.0 mL/min. The substrate temperature was about 30° C., and the chamber pressure was about 400 mTorr. The ionic liquid was N-hexylethylenediaminium bis(trifluoroethanesulfonyl)amide, [HHex][$Tf_2N$] (FIG. 1).

Example 3

Antimicrobial Effect of Polymer Coating with an Encapsulated Ionic Liquid

Figure 3A:
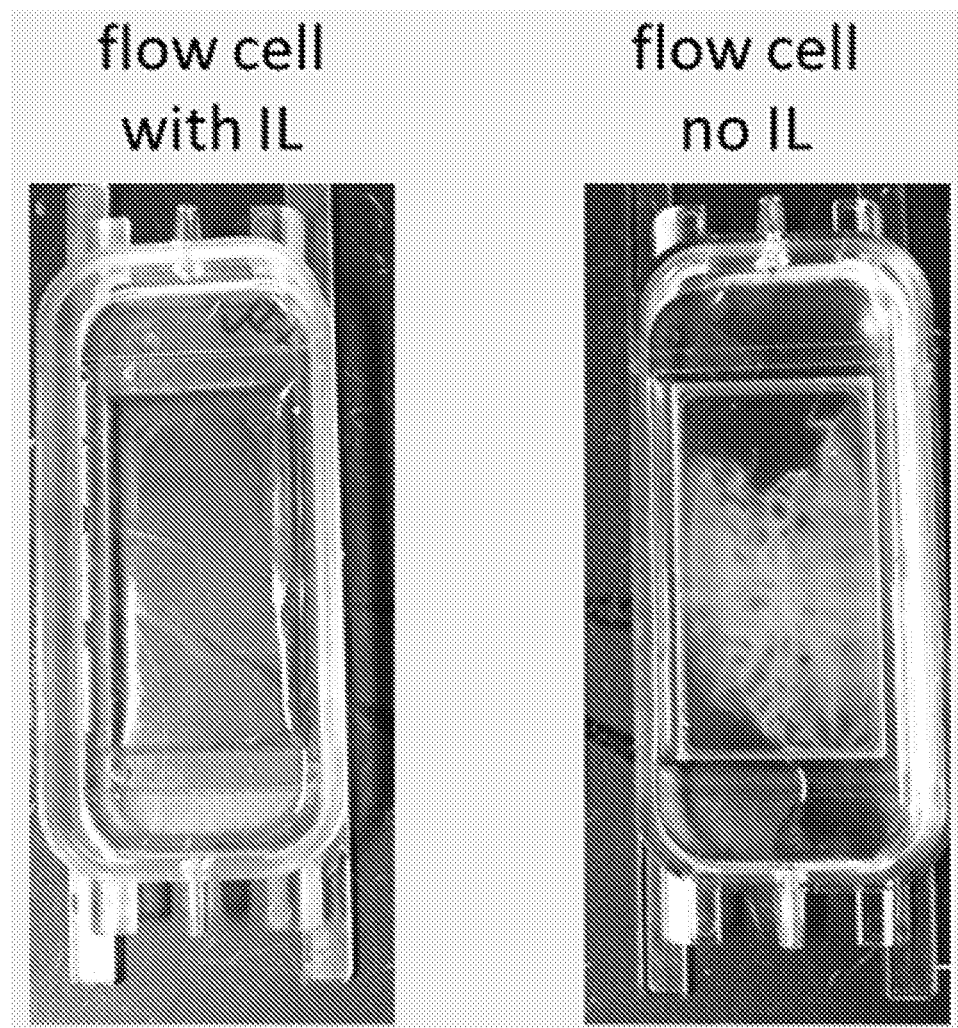
FIG. 3A shows images of flow cells treated with [HHex][Tf$_2$N] encapsulated in a polymer coating to form an ionogel (left), and without an encapsulated ionic liquid (right).
Figure 3B:
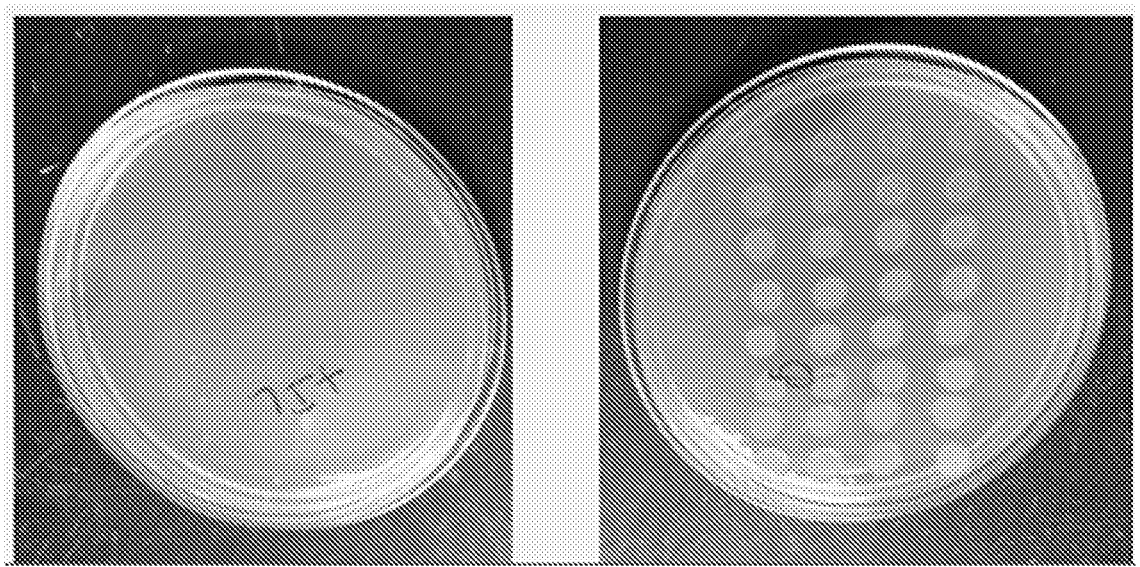
FIG. 3B shows images of bacterial growth based on the flow cells treated with [HHex][Tf$_2$N] encapsulated in a polymer coating to form an ionogel (left), and without an encapsulated ionic liquid (right).
Figure 3C:
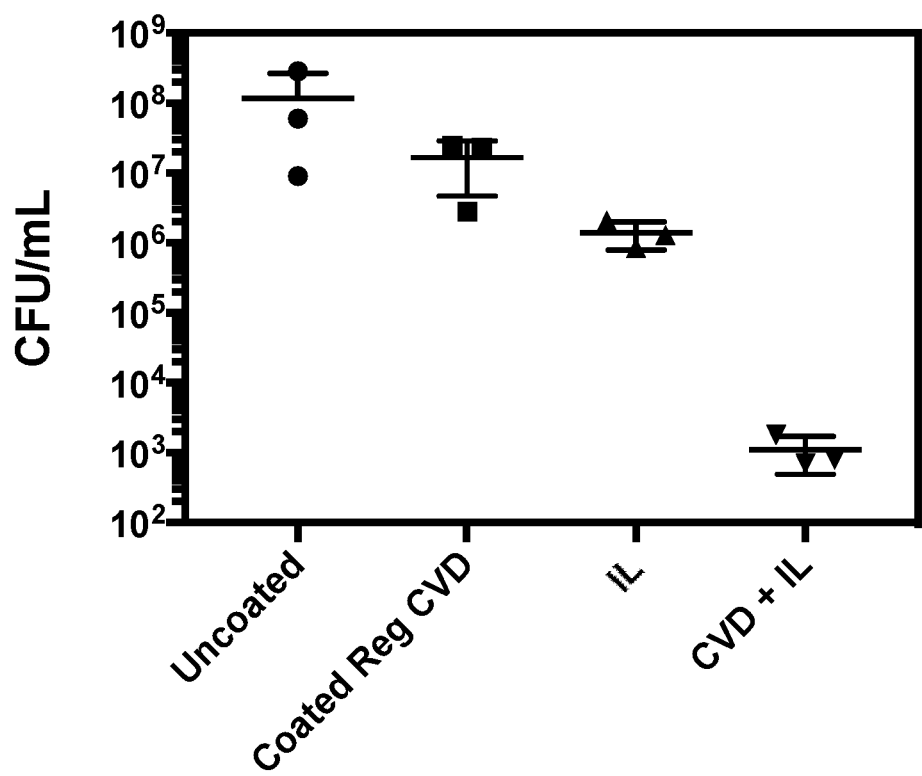
FIG. 3C shows colony counts (CFU/mL) for bacterial growth on (i) control catheters (i.e., uncoated catheters), (ii) catheters with a coating as described herein but without an encapsulated ionic liquid (coated Reg CVD), (iii) catheters with pure [HHex][Tf$_2$N], and (iv) catheters with a polymer coating as described herein with encapsulated [HHex][Tf$_2$N] (CVD+IL).

A flow cell had the bottom side CVD coated by the polymer as described in Example 2. One cell had the polymer film impregnated by an IL ([HHex][$Tf_2N$]). A medium, which had been previously inoculated with a bacterial culture (*Pseudomonas aeruginosa*), was flowed through both cells. *P. aeruginosa* is an aggressive bacterial strain with resistance to some known antibiotics. The cell containing the CVD polymer with an encapsulated task specific ionic liquid had no biofilm growth, whereas the film without an encapsulated IL exhibited the formation of a robust biofilm (FIG. 3A). The white cloudiness was due to biofilm formation. FIG. 3B shows images of the resulting bacterial growth based on the flow cells treated with [HHex][$Tf_2N$] encapsulated in a polymer coating (left), and without an encapsulated ionic liquid (right). Inductively coupled plasma (ICP) mass spectrometry experiments demonstrated a lack of ionic liquid leaching over time due to trapping in the ionogel.

Example 4

Metal Remediation with a Polymer Coating with an Encapsulated Ionic Liquid

Figure 4:
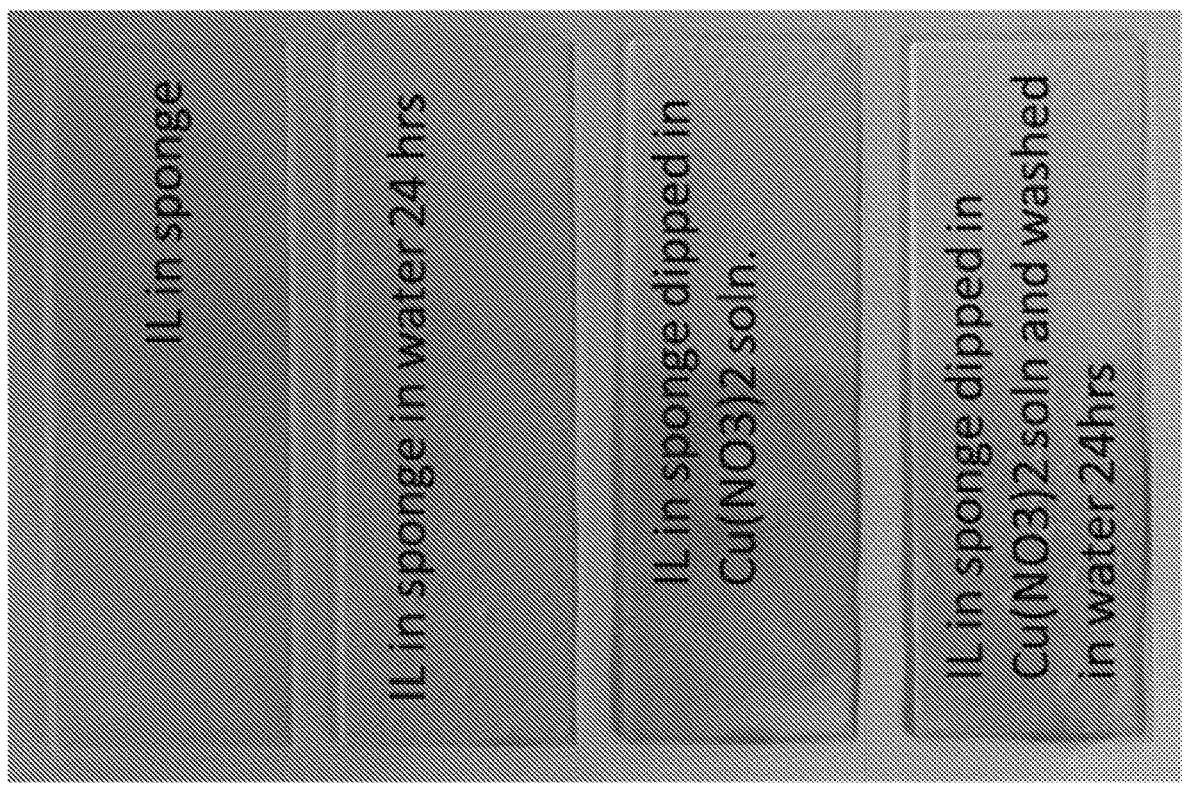
FIG. 4 shows glass slides coated with a grafted polymer coating via CVD then encapsulating a task specific ionic liquid to form an ionogel. The ionic liquid changes color upon extracting $Cu^{2+}$ from a $Cu(NO_3)_2$ solution. After a day in water the polymer and ionic liquid have not desorbed.

An example of using these bound ionogels (a polymer coating with an encapsulated ionic liquid) for metal remediation can be seen in FIG. 4. Glass slides were coated with a grafted polymer mesh via CVD then impregnated by task specific ionic liquid (see Example 2). The ionic liquid turned purple upon extracting $Cu^{2+}$ from the greenish blue $Cu(NO_3)_2$ solution. The formation of a metal complex was indicated by the color change. After a day in water the polymer and ionic liquid have not desorbed as evidenced by the similar color change upon metal complexation.

Example 5

Polymer Coating of a Catheter with an Encapsulated Ionic Liquid

Segments of RÜSCH® (Teleflex Medical) catheter were coated with a 1 μm thick film of polydimethylacrylamide crosslinked with di(ethylene glycol) divinyl ether, via iCVD polymerization. The segments were then wetted with [eth-hex-en][$Tf_2N$] to impregnate the thin film with the IL and form a metal-chelating ionogel (FIG. 5). These were then dipped in in aqueous iron(III) chloride solution to mimic iron chelation in bacterial cultures. The elemental mapping of the uncoated catheter segment indicated the presence of carbon, chlorine and oxygen in the polymer of the catheter. Upon coating of the segment with a thin polydimethylacrylamide film, a faint nitrogen signal was observed due to the nitrogen atoms in the polymer film. The ionogel of the polymer film with [eth-hex-en][$Tf_2N$] showed a stronger nitrogen signal, in addition to sulfur and fluorine signals, due to their presence in the cation and anion of the IL. The resulting ionogel upon wetting with ILs was uniform. A strong and uniform iron signal was observed after dipping in an aqueous iron(III) chloride solution, which demonstrated the chelation of iron by the ionogel. Without being bound by any theory, the ability to chelate iron ions was believed to lend the ionogel its antimicrobial activity. The presence of these elements on the catheter segments was corroborated by the Energy Dispersive Spectroscopy (EDS).

Example 6

Ionogel Coating on a Conductive Substrate

Figure 6:
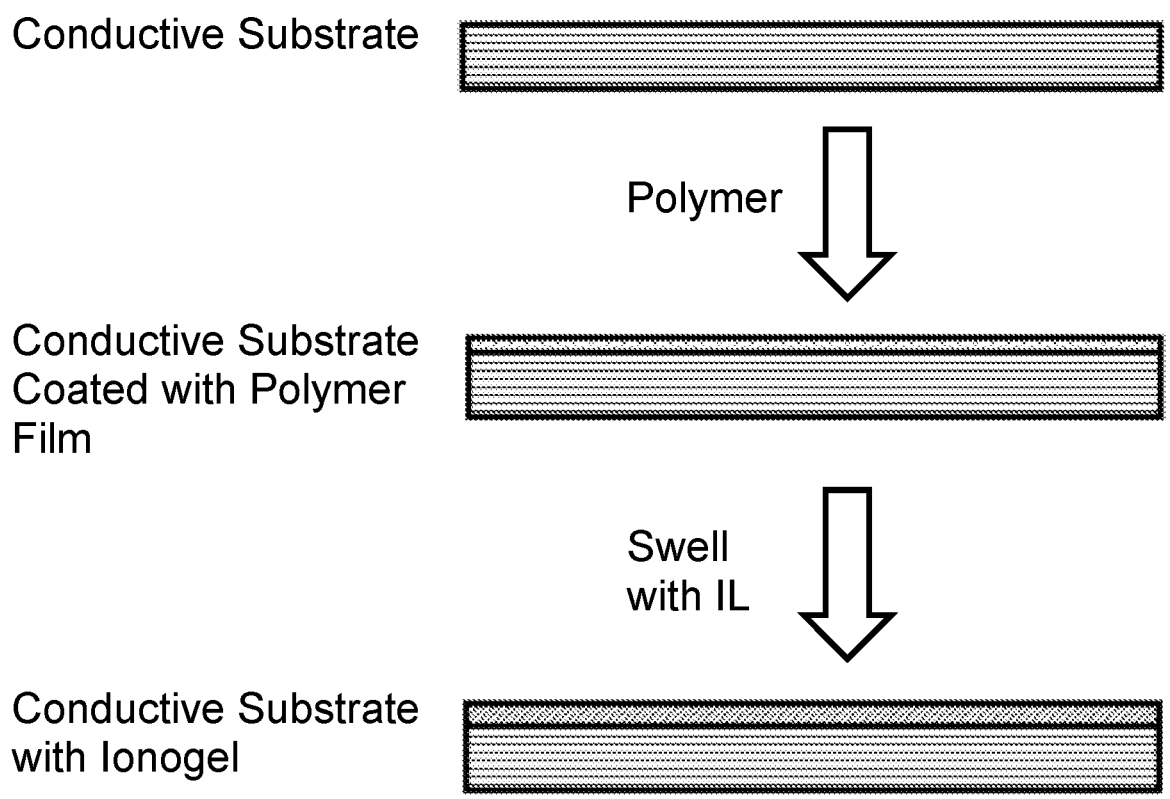
FIG. 6 shows a schematic of coating a conductive substrate to form a substrate coated with an ionogel.

The ionic liquids mentioned here can also be impregnated into polymer films deposited onto conductive substrates to form an ionogel. A conductive substrate can be in the form of a conductive strip or a conductive sheet. Thin polymer films (1-5 μm) can be deposited onto a conductive substrates via CVD, dip-coating, slot die coating, doctor blade coating, or otherwise at a speed from about 2 ft/min to about 100 ft/min. The polymer films are then impregnated by ILs via swelling of the polymer. As such, ILs are immobilized onto a conducting substrate (FIG. 6).

Figure 7:
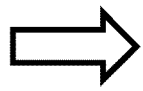
FIG. 7 shows a schematic of ionogel saturation after exposure to a flow of a contaminated solution.
Figure 7:
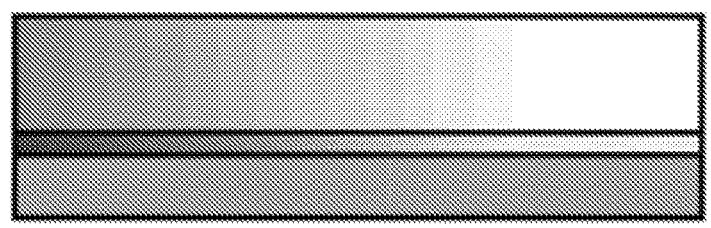
Figure 7:
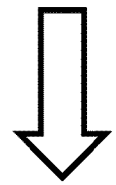
Figure 7:
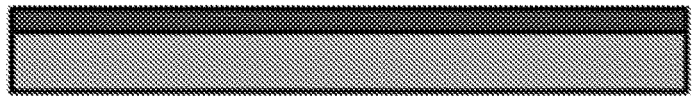
Figure 8A:
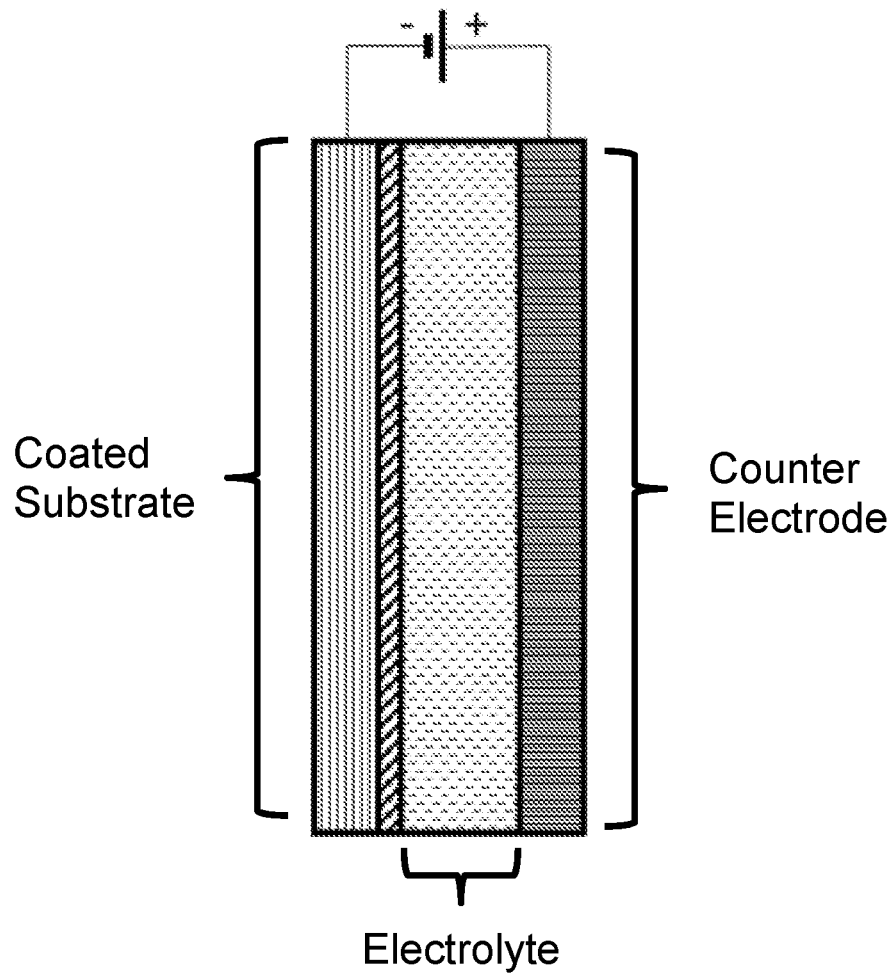
FIG. 8A shows a schematic of an electrochemical cell with a conductive substrate coated with an ionogel as the cathode, a counterelectrode as the anode, and an electrolyte solution.
Figure 8B:
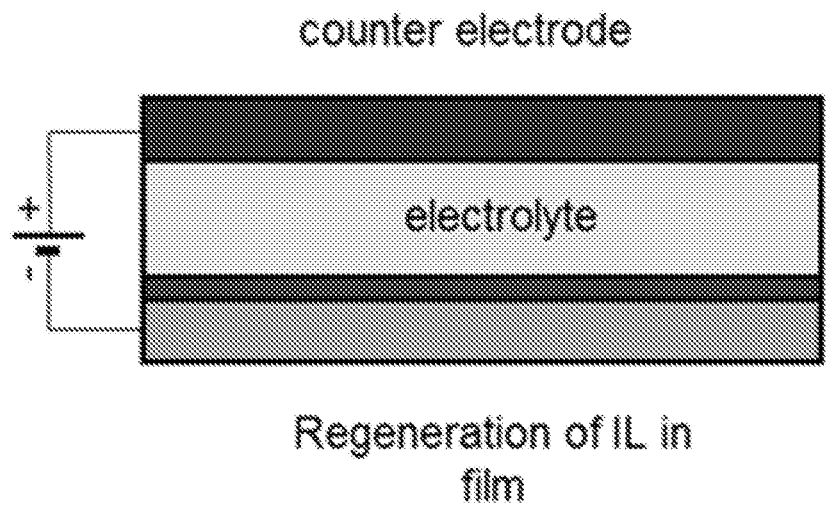
FIG. 8B shows a schematic of electroplating onto a substrate to regenerate the binding sites of an ionogel.

These coated substrates can be introduced into aqueous streams comprising a concentration of metal ions for the removal of these metal ions until saturation of the coating (FIG. 7). Upon the saturation of the ionogel by occupying all the chelation sites (FIG. 7), the metal ions can be plated onto the conductive substrate by making the coated substrate an electrode in an electrochemical cell. In this cell, the coated substrate serves as the cathode, and a counter electrode (serving as the anode) and an electrolyte solution (ionic liquid or other solutions) complete the circuit (FIGS. 8A and 8B). When the metal ions are plated onto the substrates, the IL binding (chelating) sites are regenerated for further binding. The electrochemical cell can be part of a water-treating device, or an independent device where a coated and saturated conductive substrate is removed from a water-treating device and inserted into the cell as a cathode for regeneration.

REFERENCES CITED

1) O. N. Silva et al., An anti-infective synthetic peptide with dual antimicrobial and immunomodulatory activities, *Sci. Reports*, 2016, 6, 35465.
2) S. Arora et al., Polymer Based Antimicrobial Coatings as Potential Biomaterial: A Review, *Int. J. Sci. Rev. Res.*, 2013, 23, 279
3) T. L. Lin et al., Antimicrobial coatings: a remedy for medical device-related infections, *Med. Device Technol.*, 2001, 12, 26
4) N. T. P. Phong et al., Fabrication of antibacterial water filter by coating silver nanoparticles on flexible polyurethane foams, *J. Phys.: Conference Series*, 2009, 187.
5) B. Mizrahi et al., Long-Lasting Antifouling Coating from Multi-Armed Polymer, *Langmuir*, 2013, 29, 10087.
6) J. S. Rudra et al., Antimicrobial polypeptide multilayer nanocoatings, *J. Biomater. Sci. Polym. Ed.*, 2006, 17, 1301.
7) I. Codita et al., Antimicrobial activity of copper and silver nanofilms on nosocomial bacterial species, *Roum. Arch. Microbiol. Immunol.*, 2010, 69, 204.
8) M. A. Caomagnoni et al., Antimicrobial activity and surface properties of an acrylic resin containing a biocide polymer, *Gerodontology*, 2012, 31, 220.
9) J. S. Price et al., Controlled release of antibiotic from coated orthopaedic implants, J. Biomed. Mater. Res., 1996, 30, 281.
10) P. B. Tchounwou, C. G. Yedjou, A. K. Patlolla, D. J. Sutton, Heavy Metals Toxicity and the Environment, EXS, 2012, 101, 133-164.
11) H. Bradl, Editor. Heavy Metals in the Environment: Origin, Interaction and Remediation Volume 6. London: Academic Press, 2002.
12) S. Babel, T. A. Kurniawan, Various treatment technologies to remove arsenic and mercury from contaminated groundwater: an overview, Proceedings of the First International Symposium on Southeast Asian Water Environment, Bangkok, Thailand, 2003, 24-25, 433-440.
13) J. H. Duffus, Heavy metals-a meaningless term?, Pure Appl. Chem., 2002, 74, 793-807.
14) K. C. Kang, S. S. Kim, J. W. Choi, S. H. Kwon, Competitive adsorption characteristics of $Co_{2+}$, $Ni_{2+}$, and $Cr_{2+}$ by IRN-77 cation exchange resin in synthesized wastewater, Chemosphere, 2004, 56, 131-147.
15) B. Alyüz, S. Veli, Kinetics and equilibrium studies for the removal of nickel and zinc from aqueous solutions by ion exchange resins, J. Hazard. Mater., 2009, 167, 482-488.
16) E. Sampera, M. Rodrigueza, M. A. De la Rubia, D. Prats, Removal of metal ions at low concentrations by micellar-enhanced ultrafiltration (MEUF) using sodium dodecyl sulfate (SDS) and linear alkylbenzene sulfonate (LAS), Sep. Purif., Technol., 2009, 65, 337-342.
17) Q. Chang, G. Wang, Study on the macromolecular coagulant PEX which traps heavy metals, Chem. Eng. Sci., 2007, 62, 4636-4642.
18) M. Plattes, A. Betrand, B. Schmitt, J. Sinner, F. Versraeten, J. Welfring, Removal of tungsten oxyanions from industrial wastewater by precipitation coagulation and flocculation processes, J. Hazard. Mater. 2007, 148, 613-615.
19) Barakat M. A., New trends in removing heavy metals from industrial wastewater, Arabian J. Chem., 2011, 4, 361-377.
20) R. Apiratikul, P. Pavasant, Batch and column studies of biosorption of heavy metals by Caulerpa lentillifera, Bioresour. Technol., 2008, 99, 2766-2777.
21) Y. Ku, I. L. Jung, Photocatalytic reduction of Cr(VI) in aqueous solutions by UV irradiation with the presence of titanium dioxide, Water Res., 2001, 35, 135-142.
22) M. M. Matlock, K. R. Henke, D. A. Atwood, Effectiveness of commercial reagents for heavy metal removal from water with new insights for future chelate designs, J. Hazard. Mater., 2002, 92, 129-142.
23) Y. Xu, F. Zhang, Experimental research on heavy metal wastewater treatment with dipropyl dithiophosphate, J. Hazard. Mater., 2006, 137, 1636-1642.
24) I. K. Wang, Y. T. Hung, N. K. Shammas, Advanced physicochemical treatment technologies. In: Handbook of Environmental Engineering, vol. 5, Humana, New Jersey, 2007.
25) M. L. Dietz, J. A. Dzielawa, Ion-exchange as a mode of cation transfer into room-temperature ionic liquids containing crown ethers: implications for the "greenness" of ionic liquids as diluents in liquid-liquid extraction, Chem. Commun., 2001, 2124-2125.
26) A. E. Visser, R. P. Swatloski, W. M. Reichhert, R. Mayton, S. Sheff, A. Wierzbicki, J. H. Davis Jr, R. D. Rogers, Task-specific ionic liquids for the extraction of metal ions from aqueous solutions, Chem. Commun., 2001, 135-136.
27) R. S. Kalb, Method for Producing Ionic Liquids, Ionic Solids or Mixtures thereof, 2005, WO2005/021484.
28) L. Fischer, T. Falta, G. Koellensperger, A. Stojanovic, D. Kogelnnig, M. Galanski, R. Krachler, B. K. Keppler, S. Hann, Ionic Liquids for extraction of metals and metal containing compounds from communal and industrial waste water, Water Res., 2011, 45, 4601-4614.
29) D. Depuydt, L. Liu, C. Glorieux, W. Dehaen, K. Binnemans, Homogeneous liquid-liquid extraction of metal ions with non-fluorinated bis(2-ethylhexyl)phosphate ionic liuqids having a lower critical solution temperature in combination with water, Chem. Commun., 2015, 51, 14183-14186.
30) M. A. Valdes Vergara, I. V. Lijanova, N. V. Likhanova, O. Olivares Xometl, D. Jaramillo Vigueras, A. J. Morales Ramirez, Recycling and recovery of ammonium-based ionic liquids after extraction of metal cations from aqueous solutions, Separation and Purif. Technol., 2015, 155, 110-117.
31) S. Ren et al., What are functional ionic liquids for the absorption of acidic gases, *J. Phys. Chem. B*, 2013, 117, 2482.

32) H. Q. Nimal Gunaratne et al., Ionic liquids for efficient hydrogen sulphide and thiol scavenging, *Green Chem.*, 2014, 16, 2411.
33) D. D. Jayasena et. al., Flavour Chemistry of Chicken Meat: A Review, *Asian-Australias J. Anim. Sci.*, 2013, 26, 732.
34) Liquid-Impregnated Coatings and Devices Containing the Same. US 2016/0074915 A1.
35) J. Le Bideau et al., Ionogels, ionic liquid based hybrid materials, Chem. Soc. Rev., 2011, 40, 907.
36) B. F. Gilmore, G. P. Andrews, G. Borberly, M. J. Earle, M. A. Gilea, S. P. Gorman, A. F. Lowry, M. McLaughlin, K. R. Seddon, New J. Chem., 2013, 37, 873-876.
37) T. Pennanen, *Geoderma*, 2001, 100, 91-126.
38) C. Cox, Iron and the Virulence of *Pseudomonas aeruginosa*, *Pseudomonas.*, 2004, 1-7.
39) S. Sakohara, Y. Kuriyama, K. Koboyashi, T. Gotoh, T. Iizawa, Adsorption and desorption of calcium ions by temperature swing with copolymer of thermosensitive and chelating components grafted on porous ethylene vinyl acetate disk, *Reactive & Functional Polymers*, 2013, 73, 1632-1638.
40) T. Ikeda, H. Yamaguchi, S. Tazuke, New polymeric biocides: synthesis and antibacterial activities of polycations with pendent biguanide groups, *Antimicrob. Agents Chemother.*, 1984, 26, 139-144.

INCORPORATION BY REFERENCE

All US and PCT patent application publications and US patents cited herein are hereby incorporated by reference in their entirety as if each individual publication or patent was specifically and individually indicated to be incorporated by reference. In case of conflict, the present application, including any definitions herein, will control.
Equivalents
While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of coating a surface of an object, a device, or an assembly, comprising the steps of:
(a) providing in a partially evacuated vessel an object, a device, or an assembly comprising a surface;
(b) heating or irradiating a free radical initiator, thereby producing a gaseous free radical initiator;
(c) introducing into the partially evacuated vessel one or more gaseous monomers and the gaseous free radical initiator, thereby forming a cross-linked coating on the surface; and
(d) contacting the cross-linked coating with an ionic liquid comprising a cation and an anion; thereby forming the coating on the surface of the object, the device, or the assembly;
wherein the cation is represented by:
structural formula I:

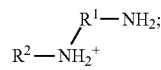

wherein, independently for each occurrence:

$R^1$ is —$(C(R)_2)_n$—;

n is 2, or 3;

$R^2$ is —$(C(R)_2)_m$-R";

m is 1, 2, 3, 4, 5, 6, 7, 8, 9, or 10; and

R is H, F, $C_1$-$C_3$ alkyl, or $C_1$-$C_3$ fluoroalkyl;

R' is H, F, $C_1$-$C_8$ alkyl, or $C_1$-$C_8$ fluoroalkyl; and

R" is H, F, $C_1$-$C_3$ alkyl, $C_1$-$C_3$ fluoroalkyl, $C_1$-$C_3$ alkyloxy, $C_1$-$C_3$ fluoroalkyloxy, $C_6$-$C_{10}$ aryl, $C_2$-$C_8$ alkenyl or $C_2$-$C_8$ fluoroalkenyl; wherein each instance of $C_6$-$C_{10}$ aryl is optionally substituted with one, two, three, four or five substituents independently selected from the group consisting of F, $C_1$-$C_3$ alkyl, $C_1$-$C_3$ fluoroalkyl, $C_1$-$C_3$ alkyloxy, and $C_1$-$C_3$ fluoroalkyloxy, or structural formula II:

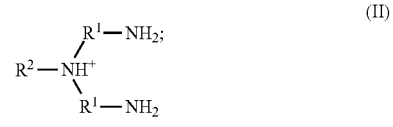

wherein, independently for each occurrence:

$R^1$ is —$(C(R)_2)_n$—;

n is 2, or 3;

$R^2$ is —$(C(R')_2)_m$-R";

m is 1, 2, 3, 4, 5, 6, 7, 8, 9, or 10; and

R is H, F, $C_1$-$C_3$ alkyl, or $C_1$-$C_3$ fluoroalkyl;

R' is H, F, $C_1$-$C_8$ alkyl, or $C_1$-$C_8$ fluoroalkyl; and

R" is H, F, $C_1$-$C_3$ alkyl, $C_1$-$C_3$ fluoroalkyl, $C_1$-$C_3$ alkyloxy, $C_1$-$C_3$ fluoroalkyloxy, $C_6$-$C_{10}$ aryl, $C_2$-$C_8$ alkenyl or $C_2$-$C_8$ fluoroalkenyl; wherein each instance of $C_6$-$C_{10}$ aryl is optionally substituted with one, two, three, four or five substituents independently selected from the group consisting of F, $C_1$-$C_3$ alkyl, $C_1$-$C_3$ fluoroalkyl, $C_1$-$C_3$ alkyloxy, and $C_1$-$C_3$ fluoroalkyloxy.

2. The method of claim 1, wherein the cation is represented by structural formula I:

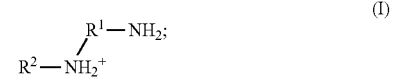

wherein, independently for each occurrence:

$R^1$ is —$(C(R)_2)_n$—;

n is 2, or 3;

$R^2$ is —$(C(R')_2)_m$-R";

m is 1, 2, 3, 4, 5, 6, 7, 8, 9, or 10; and

R is H, F, $C_1$-$C_3$ alkyl, or $C_1$-$C_3$ fluoroalkyl;

R' is H, F, $C_1$-$C_8$ alkyl, or $C_1$-$C_8$ fluoroalkyl; and

R" is H, F, $C_1$-$C_3$ alkyl, $C_1$-$C_3$ fluoroalkyl, $C_1$-$C_3$ alkyloxy, $C_1$-$C_3$ fluoroalkyloxy, $C_6$-$C_{10}$ aryl, $C_2$-$C_8$ alkenyl or $C_2$-$C_8$ fluoroalkenyl; wherein each instance of $C_6$-$C_{10}$ aryl is optionally substituted with one, two, three, four or five substituents independently selected from the group consisting of F, $C_1$-$C_3$ alkyl, $C_1$-$C_3$ fluoroalkyl, $C_1$-$C_3$ alkyloxy, and $C_1$-$C_3$ fluoroalkyloxy.

3. The method of claim 1, wherein the the cation is represented by structural formula II:

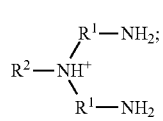

(II)

wherein, independently for each occurrence:
R$^1$ is —(C(R)$_2$)$_n$—;
n is 2, or 3;
R$^2$ is —(C(R')$_2$)$_m$-R";
m is 1, 2, 3, 4, 5, 6, 7, 8, 9, or 10; and
R is H, F, C$_1$-C$_3$ alkyl, or C$_1$-C$_3$ fluoroalkyl;
R' is H, F, C$_1$-C$_8$ alkyl, or C$_1$-C$_8$ fluoroalkyl; and
R" is H, F, C$_1$-C$_3$ alkyl, C$_1$-C$_3$ fluoroalkyl, C$_1$-C$_3$ alkyloxy, C$_1$-C$_3$ fluoroalkyloxy, C$_6$-C$_{10}$ aryl, C$_2$-C$_8$ alkenyl or C$_2$-C$_8$ fluoroalkenyl; wherein each instance of C$_6$-C$_{10}$ aryl is optionally substituted with one, two, three, four or five substituents independently selected from the group consisting of F, C$_1$-C$_3$ alkyl, C$_1$-C$_3$ fluoroalkyl, C$_1$-C$_3$ alkyloxy, and C$_1$-C$_3$ fluoroalkyloxy.

4. The method of claim 1, wherein the ionic liquid comprises water.

5. The method of claim 1, wherein the free radical initiator is selected from the group consisting of a peroxide, an aryl ketone, and an azo compound.

6. The method of claim 1, wherein the free radical initiator comprises triethylamine.

7. The method of claim 1, wherein the free radical initiator is an azo compound selected from the group consisting of 4,4'-Azobis(4-cyanovaleric acid), 4,4'-Azobis(4-cyanovaleric acid), 1,1'-Azobis(cyclohexanecarbonitrile), 2,2'-Azobis(2-methylpropionamidine) dihydrochloride, 2,2'-Azobis(2-methylpropionitrile), and 2,2'-Azobis(2-methylpropionitrile).

8. The method of claim 1, wherein the free radical initiator is a peroxide selected from the group consisting of tent-butyl hydroperoxide, tent-butyl peracetate, cumene hydroperoxide, dicumyl peroxide, benzoyl peroxide, tent-amyl peroxide, tent-butyl peroxide, and tent-butyl peroxybenzoate.

9. The method of claim 1, wherein the monomer is at least one of an acrylate, an acrylamide, a siloxane, a silane, and a vinyl compound.

10. The method of claim 1, wherein the one or more monomers are selected from the group consisting of methyl methacrylate, butyl acrylate, glycidal methacrylate, hydroxyl ethyl methacrylate, ethylene glycol diacrylate, propargyl methacrylate, pentafluorophenyl methacrylate, hydroxyethyl methacrylate, cyclohexyl methacrylate, methacrylic acid-co-ethyl acrylate, 1H,1H,6H,6H-perfluorohexyldiacrylate, 1H,2H,2H-perfluorooctyl acrylate, 1H,2H,2H-perfluorodecyl acrylate, N,N-dimethylacrylamide, polydimethylacrylamide, 2-vinyl pyridine, 4-vinyl pyridine, p-divinylbenzene, m-divinylbenzene, trivinylytrimethylcyclotri siloxane, tetravinyltetramethylcyclotetra-siloxane, trichlorovinylsilane, di(ethylene glycol) divinyl ether, xylylene, vinylene, dimethylaminomethyl styrene, pyrrole, 3-thiopheneacetic acid, and copolymers thereof.

11. The method of claim 1, wherein the one or more monomers are selected from N,N-dimethylacrylamide, polydimethylacrylamide, trichlorovinylsilane, and di(ethylene glycol) divinyl ether.

12. The method of claim 1, wherein each n is 2.

13. The method of claim 1, wherein each n is 2; and each R is H.

14. The method of claim 1, wherein each m is 6; and each R" is H.

15. The method of claim 1, wherein each R$^2$ is 2-ethylhexyl.

16. The method of claim 1, wherein the anion is boron tetrafluoride, phosphorus tetrafluoride, phosphorus hexafluoride, alkylsulfonate, fluoroalkylsulfonate, arylsulfonate, bis(alkyl sulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin.

17. The method of claim 1, wherein the anion is boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

18. The method of claim 1, wherein the anion is bis(trifluoromethanesulfonyl)amide or (trifluoromethanesulfonyl)(trifluoroacetyl)amide.

19. The method of claim 5, wherein the anion is boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin.

20. The method of claim 5, wherein the anion is boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

21. The method of claim 5, wherein the anion is bis(trifluoromethanesulfonyl)amide or (trifluoromethanesulfonyl)(trifluoroacetyl)amide.

22. The method of claim 10, wherein the anion is boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin.

23. The method of claim 10, wherein the anion is boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

24. The method of claim 10, wherein the anion is bis(trifluoromethanesulfonyl)amide or (trifluoromethanesulfonyl)(trifluoroacetyl)amide.

* * * * *